United States Patent
Wilson et al.

(10) Patent No.: US 11,820,747 B2
(45) Date of Patent: Nov. 21, 2023

(54) PPARG INVERSE AGONISTS AND USES THEREOF

(71) Applicant: Flare Therapeutics Inc., Cambridge, MA (US)

(72) Inventors: Jonathan E. Wilson, Arlington, MA (US); James E. Audia, Chicago, IL (US); Jacob I. Stuckey, Framingham, MA (US)

(73) Assignee: Flare Therapeutics Inc., Cambridge, MA (US)

( * ) Notice: Subject to any disclaimer, the term of this patent is extended or adjusted under 35 U.S.C. 154(b) by 0 days.

(21) Appl. No.: 18/130,121

(22) Filed: Apr. 3, 2023

(65) Prior Publication Data

US 2023/0331678 A1 Oct. 19, 2023

Related U.S. Application Data

(63) Continuation of application No. PCT/CN2022/129034, filed on Nov. 1, 2022.

(60) Provisional application No. 63/347,671, filed on Jun. 1, 2022, provisional application No. 63/274,596, filed on Nov. 2, 2021.

(51) Int. Cl.
*C07D 215/233* (2006.01)
*A61P 35/00* (2006.01)

(52) U.S. Cl.
CPC .......... *C07D 215/233* (2013.01); *A61P 35/00* (2018.01); *C07B 2200/13* (2013.01)

(58) Field of Classification Search
CPC .............. C07D 215/233; A61P 35/00
See application file for complete search history.

(56) References Cited

U.S. PATENT DOCUMENTS

| | | | |
|---|---|---|---|
| 4,992,464 A | 2/1991 | Brooks et al. | |
| 4,994,474 A | 2/1991 | Gubin et al. | |
| 5,017,579 A | 5/1991 | Gillard et al. | |
| 5,474,994 A | 12/1995 | Leonardi et al. | |
| 5,605,896 A | 2/1997 | Leonardi et al. | |
| 6,500,853 B1 | 12/2002 | Seehra et al. | |
| 7,732,446 B1 | 6/2010 | Gwaltney et al. | |
| 8,440,692 B2 | 5/2013 | Kuo et al. | |
| 8,987,301 B2 | 3/2015 | Jonczyk et al. | |
| 10,596,145 B2 * | 3/2020 | Ye | A61K 31/4188 |
| 2004/0167151 A1 | 8/2004 | Lee et al. | |
| 2005/0032832 A1 | 2/2005 | Kuo et al. | |
| 2005/0080024 A1 | 4/2005 | Tucker et al. | |
| 2005/0137234 A1 | 6/2005 | Bressi et al. | |
| 2005/0261167 A1 | 11/2005 | Chan et al. | |
| 2005/0267108 A1 | 12/2005 | Hsieh et al. | |
| 2006/0025337 A1 | 2/2006 | Sinclair et al. | |
| 2006/0084135 A1 | 4/2006 | Howitz et al. | |
| 2007/0099826 A1 | 5/2007 | Wong et al. | |
| 2007/0267959 A1 | 11/2007 | Ragini et al. | |
| 2008/0004297 A1 | 1/2008 | Cai et al. | |
| 2008/0161247 A1 | 7/2008 | Surolia et al. | |
| 2008/0188467 A1 | 8/2008 | Wong et al. | |
| 2008/0261898 A1 | 10/2008 | Liao et al. | |
| 2008/0280879 A1 | 11/2008 | Brickner et al. | |
| 2009/0163545 A1 | 6/2009 | Goldfarb | |
| 2009/0264384 A1 | 10/2009 | Didsbury et al. | |
| 2010/0016352 A1 | 1/2010 | Li et al. | |
| 2010/0267132 A1 | 10/2010 | McPhail et al. | |
| 2011/0182812 A1 | 7/2011 | Szardenings et al. | |
| 2011/0224155 A1 | 9/2011 | Tachdjian et al. | |
| 2012/0053347 A1 | 3/2012 | Colburn et al. | |
| 2012/0165370 A1 | 6/2012 | Tang et al. | |
| 2013/0018079 A1 | 1/2013 | Weibel et al. | |
| 2013/0112948 A1 | 5/2013 | Jung et al. | |
| 2013/0225580 A1 | 8/2013 | Chen et al. | |
| 2013/0281399 A1 | 10/2013 | McLure et al. | |
| 2013/0310555 A1 | 11/2013 | Chong | |

(Continued)

FOREIGN PATENT DOCUMENTS

| CA | 2066094 A1 | 10/1992 |
|---|---|---|
| CN | 101357902 A | 2/2009 |

(Continued)

OTHER PUBLICATIONS

Hino et al., Nonsteroidal Antiinflammatory Agents. III. : Synthesis of the Metabolites of 10, 11-Dihydro-8, a-dimethyl-11-oxodibenz[b, floxepin-2-acetic Acid (Bermoprofen). Chem. Pharm. Bull. 1988;36(9):3462-7.
Li et al., An unexpected synthesis and application of ethyl 2,4-bis(chloromethyl)-6-iodoquinoline-3-carboxylate. Res. Chem. Inter. Jan. 29, 2020;46(4):2215-28.
Roy et al., Anticancer Evaluation of Azetidinone and Thiazolidinone Derivatives of Quinolone. Int. J. Chem. Sci. 2005;3(3):529-36.
Ye, Regulation of PPARgamma function by TNF-alpha. Biochem Biophys Res Commun. Sep. 26, 2008;374(3):405-8.

(Continued)

*Primary Examiner* — D Margaret M Seaman
(74) *Attorney, Agent, or Firm* — McCarter & English, LLP; Michael J. DeGrazia

(57) ABSTRACT

Provided are compounds of Formula (I):

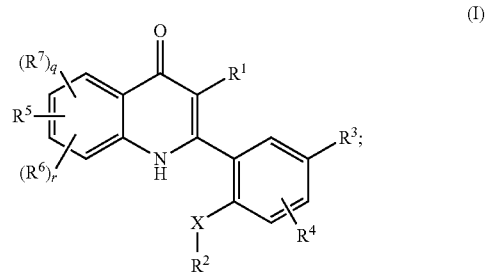

(I)

and pharmaceutically acceptable salts and compositions thereof, which are useful for treating a variety of conditions associated with PPARG.

11 Claims, 2 Drawing Sheets

(56) References Cited

U.S. PATENT DOCUMENTS

| | | | |
|---|---|---|---|
| 2014/0005168 | A1 | 1/2014 | Do et al. |
| 2014/0140956 | A1 | 5/2014 | Fairfax et al. |
| 2014/0142102 | A1 | 5/2014 | Fairfax et al. |
| 2015/0166492 | A1 | 6/2015 | Cuervo et al. |
| 2017/0008863 | A1 | 1/2017 | Chong |
| 2017/0069850 | A1 | 3/2017 | Hwang et al. |
| 2017/0207397 | A1 | 7/2017 | Lee et al. |
| 2017/0298040 | A1 | 10/2017 | Bennett et al. |
| 2018/0179159 | A1 | 6/2018 | Becknell et al. |
| 2018/0334454 | A1 | 11/2018 | Lanman et al. |
| 2019/0115543 | A1 | 4/2019 | Kim et al. |
| 2019/0152913 | A1 | 5/2019 | Becknell et al. |
| 2019/0284149 | A1 | 9/2019 | Song et al. |
| 2020/0330449 | A1 | 10/2020 | Chein et al. |

FOREIGN PATENT DOCUMENTS

| | | | |
|---|---|---|---|
| CN | 101444499 | A | 6/2009 |
| CN | 102675200 | A | 9/2012 |
| CN | 103877078 | A | 6/2014 |
| CN | 103880707 | A | 6/2014 |
| CN | 103961348 | A | 8/2014 |
| CN | 104725363 | A | 6/2015 |
| CN | 104744435 | A | 7/2015 |
| CN | 105085482 | A | 11/2015 |
| CN | 105481765 | A | 4/2016 |
| CN | 105669546 | A | 6/2016 |
| CN | 105732464 | A | 7/2016 |
| CN | 105732591 | A | 7/2016 |
| CN | 105936635 | A | 9/2016 |
| CN | 106946775 | A | 7/2017 |
| CN | 107021958 | A | 8/2017 |
| CN | 107021964 | A | 8/2017 |
| CN | 107661333 | A | 2/2018 |
| CN | 107759620 | A | 3/2018 |
| CN | 107773562 | A | 3/2018 |
| CN | 108558753 | A | 9/2018 |
| CN | 108610286 | A | 10/2018 |
| CN | 108623560 | A | 10/2018 |
| CN | 108623562 | A | 10/2018 |
| CN | 109608504 | A | 4/2019 |
| CN | 105982884 | B | 5/2019 |
| CN | 110372588 | A | 10/2019 |
| CN | 110429187 | A | 11/2019 |
| CN | 110498784 | A | 11/2019 |
| CN | 110790752 | A | 2/2020 |
| CN | 107522657 | B | 6/2020 |
| CZ | 304527 | B6 | 6/2014 |
| DE | 1942661 | A1 | 2/1970 |
| EP | 0302792 | A2 | 2/1989 |
| EP | 0302793 | A2 | 2/1989 |
| EP | 0341104 | A2 | 11/1989 |
| EP | 0412848 | A2 | 2/1991 |
| EP | 0453210 | A2 | 10/1991 |
| EP | 0466452 | A2 | 1/1992 |
| EP | 0470794 | A1 | 2/1992 |
| EP | 0470795 | A1 | 2/1992 |
| EP | 0487252 | A1 | 5/1992 |
| EP | 0516392 | A2 | 12/1992 |
| EP | 0520723 | A1 | 12/1992 |
| EP | 0520724 | A1 | 12/1992 |
| EP | 0539066 | A1 | 4/1993 |
| EP | 0567828 | A2 | 11/1993 |
| EP | 0786460 | A2 | 7/1997 |
| EP | 0811613 | A1 | 12/1997 |
| EP | 0856310 | A2 | 8/1998 |
| EP | 0856316 | A1 | 8/1998 |
| EP | 1172422 | A2 | 1/2002 |
| EP | 1336602 | A1 | 8/2003 |
| EP | 1938841 | A2 | 7/2008 |
| EP | 3208864 | A1 | 8/2017 |
| EP | 3613751 | A1 | 2/2020 |
| FR | 2636327 | A1 | 3/1990 |
| FR | 2956816 | A1 | 9/2011 |
| JP | S58-219166 | A | 12/1983 |
| JP | S60-004170 | A | 1/1985 |
| JP | H06-073047 | A | 3/1994 |
| JP | H08-301849 | A | 11/1996 |
| JP | 2004-244362 | A | 9/2004 |
| JP | 2005-078888 | A | 3/2005 |
| JP | 2005-078995 | A | 3/2005 |
| JP | 2005-162657 | A | 6/2005 |
| JP | 2006-096687 | A | 4/2006 |
| JP | 2007-230145 | A | 9/2007 |
| KR | 20100046905 | A | 5/2010 |
| MY | 138338 | A | 5/2009 |
| WO | WO-1991/007404 | A1 | 5/1991 |
| WO | WO-1993/017007 | A1 | 9/1993 |
| WO | WO-1993/024501 | A1 | 12/1993 |
| WO | WO-1994/000450 | A1 | 1/1994 |
| WO | WO-1994/001408 | A1 | 1/1994 |
| WO | WO-1994/002145 | A2 | 2/1994 |
| WO | WO-1994/012478 | A1 | 6/1994 |
| WO | WO-1995/013266 | A1 | 5/1995 |
| WO | WO-1996/000901 | A1 | 1/1996 |
| WO | WO-1996/010563 | A1 | 4/1996 |
| WO | WO-1996/041800 | A1 | 12/1996 |
| WO | WO-1997/014419 | A1 | 4/1997 |
| WO | WO-1997/016447 | A1 | 5/1997 |
| WO | WO-2007/016525 | A2 | 2/2000 |
| WO | WO-2000/016774 | A1 | 3/2000 |
| WO | WO-2000/053313 | A2 | 9/2000 |
| WO | WO-2001/049685 | A2 | 7/2001 |
| WO | WO-2001/080855 | A1 | 11/2001 |
| WO | WO-2001/081340 | A2 | 11/2001 |
| WO | WO-2002/000623 | A2 | 1/2002 |
| WO | WO-2002/009702 | A2 | 2/2002 |
| WO | WO-2002/026220 | A2 | 4/2002 |
| WO | WO-2002/026713 | A1 | 4/2002 |
| WO | WO-2002/026730 | A2 | 4/2002 |
| WO | WO-2002/070515 | A2 | 9/2002 |
| WO | WO-2003/006440 | A2 | 1/2003 |
| WO | WO-2003/010140 | A2 | 2/2003 |
| WO | WO-2003/010141 | A2 | 2/2003 |
| WO | WO-2003/011872 | A1 | 2/2003 |
| WO | WO-2003/014377 | A2 | 2/2003 |
| WO | WO-2003/016309 | A1 | 2/2003 |
| WO | WO-2003/039538 | A1 | 5/2003 |
| WO | WO-2003/089423 | A2 | 10/2003 |
| WO | WO-2003/094928 | A1 | 11/2003 |
| WO | WO-2004/003103 | A1 | 1/2004 |
| WO | WO-2004/030635 | A2 | 4/2004 |
| WO | WO-2004/031161 | A1 | 4/2004 |
| WO | WO-2004/035047 | A1 | 4/2004 |
| WO | WO-2004/055003 | A1 | 7/2004 |
| WO | WO-2004/089947 | A2 | 10/2004 |
| WO | WO-2004/105779 | A2 | 12/2004 |
| WO | WO-2005/002672 | A2 | 1/2005 |
| WO | WO-2005/023807 | A2 | 3/2005 |
| WO | WO-2005/028478 | A1 | 3/2005 |
| WO | WO-2005/040163 | A1 | 5/2005 |
| WO | WO-2005/042712 | A2 | 5/2005 |
| WO | WO-2005/065691 | A1 | 7/2005 |
| WO | WO-2005/087227 | A1 | 9/2005 |
| WO | WO-2005/090282 | A1 | 9/2005 |
| WO | WO-2006/004722 | A2 | 1/2006 |
| WO | WO-2006/021448 | A1 | 3/2006 |
| WO | WO-2006/024535 | A1 | 3/2006 |
| WO | WO-2006/039718 | A2 | 4/2006 |
| WO | WO-2006/050236 | A2 | 5/2006 |
| WO | WO-2006/074147 | A2 | 7/2006 |
| WO | WO-2006/076681 | A2 | 7/2006 |
| WO | WO-2006/078891 | A2 | 7/2006 |
| WO | WO-2006/108107 | A1 | 10/2006 |
| WO | WO-2006/133353 | A2 | 12/2006 |
| WO | WO-2007/002781 | A2 | 1/2007 |
| WO | WO-2007/042325 | A1 | 4/2007 |
| WO | WO-2007/070986 | A1 | 6/2007 |
| WO | WO-2007/076092 | A2 | 7/2007 |
| WO | WO-2007/079666 | A1 | 7/2007 |
| WO | WO-2007/083875 | A2 | 7/2007 |
| WO | WO-2007/106537 | A2 | 9/2007 |
| WO | WO-2007/110801 | A2 | 10/2007 |
| WO | WO-2007/112322 | A2 | 10/2007 |

(56) References Cited

FOREIGN PATENT DOCUMENTS

| | | |
|---|---|---|
| WO | WO-2007/125405 A2 | 11/2007 |
| WO | WO-2007/134169 A2 | 11/2007 |
| WO | WO-2007/147217 A1 | 12/2007 |
| WO | WO-2007/147883 A1 | 12/2007 |
| WO | WO-2008/011109 A2 | 1/2008 |
| WO | WO-2008/017710 A1 | 2/2008 |
| WO | WO-2008/028427 A1 | 3/2008 |
| WO | WO-2008/034815 A1 | 3/2008 |
| WO | WO-2008/048981 A2 | 4/2008 |
| WO | WO-2008/058402 A1 | 5/2008 |
| WO | WO-2008/061208 A2 | 5/2008 |
| WO | WO-2008/070176 A1 | 6/2008 |
| WO | WO-2008/073957 A2 | 6/2008 |
| WO | WO-2008/074068 A1 | 6/2008 |
| WO | WO-2008/089439 A2 | 7/2008 |
| WO | WO-2008/092231 A1 | 8/2008 |
| WO | WO-2008/116029 A1 | 9/2008 |
| WO | WO-2008/121407 A1 | 10/2008 |
| WO | WO-2008/141013 A1 | 11/2008 |
| WO | WO-2008/142384 A1 | 11/2008 |
| WO | WO-2008/154221 A2 | 12/2008 |
| WO | WO-2009/018219 A2 | 2/2009 |
| WO | WO-2009/026166 A2 | 2/2009 |
| WO | WO-2009/026176 A2 | 2/2009 |
| WO | WO-2009/040377 A2 | 4/2009 |
| WO | WO-2009/102498 A1 | 8/2009 |
| WO | WO-2009/117335 A2 | 9/2009 |
| WO | WO-2009/129335 A2 | 10/2009 |
| WO | WO-2009/129372 A1 | 10/2009 |
| WO | WO-2009/134973 A1 | 11/2009 |
| WO | WO-2010/011836 A2 | 1/2010 |
| WO | WO-2010/020521 A1 | 2/2010 |
| WO | WO-2010/026771 A1 | 3/2010 |
| WO | WO-2010/037127 A1 | 4/2010 |
| WO | WO-2010/037129 A1 | 4/2010 |
| WO | WO-2010/077680 A2 | 7/2010 |
| WO | WO-2010/083444 A1 | 7/2010 |
| WO | WO-2010/106436 A2 | 9/2010 |
| WO | WO-2010/107765 A1 | 9/2010 |
| WO | WO-2010/107768 A1 | 9/2010 |
| WO | WO-2010/108187 A2 | 9/2010 |
| WO | WO-2010/127208 A1 | 11/2010 |
| WO | WO-2010/129553 A1 | 11/2010 |
| WO | WO-2010/151740 A2 | 12/2010 |
| WO | WO-2011/023287 A1 | 3/2011 |
| WO | WO-2011/054433 A1 | 5/2011 |
| WO | WO-2011/075699 A2 | 6/2011 |
| WO | WO-2011/097607 A1 | 8/2011 |
| WO | WO-2011/111880 A1 | 9/2011 |
| WO | WO-2011/140488 A1 | 11/2011 |
| WO | WO-2012/003271 A1 | 1/2012 |
| WO | WO-2012/003274 A1 | 1/2012 |
| WO | WO-2012/009519 A1 | 1/2012 |
| WO | WO-2012/015914 A2 | 2/2012 |
| WO | WO-2012/021837 A2 | 2/2012 |
| WO | WO-2012/024620 A2 | 2/2012 |
| WO | WO-2012/069856 A1 | 5/2012 |
| WO | WO-2012/102405 A1 | 8/2012 |
| WO | WO-2012/135016 A2 | 10/2012 |
| WO | WO-2012/154888 A1 | 11/2012 |
| WO | WO-2012/163489 A1 | 12/2012 |
| WO | WO-2012/163490 A1 | 12/2012 |
| WO | WO-2012/170371 A1 | 12/2012 |
| WO | WO-2013/002879 A1 | 1/2013 |
| WO | WO-2013/002880 A1 | 1/2013 |
| WO | WO-2013/010869 A1 | 1/2013 |
| WO | WO-2013/020184 A1 | 2/2013 |
| WO | WO-2013/022740 A2 | 2/2013 |
| WO | WO-2013/049352 A2 | 4/2013 |
| WO | WO-2013/053372 A1 | 7/2013 |
| WO | WO-2013/097753 A1 | 10/2013 |
| WO | WO-2013/146437 A1 | 10/2013 |
| WO | WO-2013/158928 A2 | 10/2013 |
| WO | WO-2013/175281 A1 | 11/2013 |
| WO | WO-2013/191112 A1 | 12/2013 |
| WO | WO-2014/018741 A1 | 1/2014 |
| WO | WO-2014/067603 A1 | 5/2014 |
| WO | WO-2014/071134 A1 | 5/2014 |
| WO | WO-2014/087165 A1 | 6/2014 |
| WO | WO-2014/139388 A1 | 9/2014 |
| WO | WO-2014/179785 A1 | 11/2014 |
| WO | WO-2015/009812 A2 | 1/2015 |
| WO | WO-2015/031608 A1 | 3/2015 |
| WO | WO-2015/031613 A1 | 3/2015 |
| WO | WO-2015/035051 A1 | 3/2015 |
| WO | WO-2015/086523 A1 | 6/2015 |
| WO | WO-2015/169180 A1 | 11/2015 |
| WO | WO-2015/172076 A1 | 11/2015 |
| WO | WO-2016/009076 A1 | 1/2016 |
| WO | WO-2016/050921 A1 | 4/2016 |
| WO | WO-2016/074757 A1 | 5/2016 |
| WO | WO-2016/094730 A1 | 6/2016 |
| WO | WO-2016/141855 A1 | 9/2016 |
| WO | WO-2016/153432 A1 | 9/2016 |
| WO | WO-2016/196742 A1 | 12/2016 |
| WO | WO-2017/012579 A1 | 1/2017 |
| WO | WO-2017/028797 A1 | 2/2017 |
| WO | WO-2017/031427 A1 | 2/2017 |
| WO | WO-2017/061957 A1 | 4/2017 |
| WO | WO-2017/072283 A1 | 5/2017 |
| WO | WO-2017/103615 A1 | 6/2017 |
| WO | WO-2017/141116 A1 | 8/2017 |
| WO | WO-2017/181379 A1 | 10/2017 |
| WO | WO-2017/205538 A1 | 11/2017 |
| WO | WO-2018/009622 A1 | 1/2018 |
| WO | WO-2018/037295 A1 | 3/2018 |
| WO | WO-2018/054711 A1 | 3/2018 |
| WO | WO-2018/064498 A1 | 4/2018 |
| WO | WO-2018/066812 A1 | 4/2018 |
| WO | WO-2018/119183 A2 | 6/2018 |
| WO | WO-2018/121434 A1 | 7/2018 |
| WO | WO-2018/137683 A1 | 8/2018 |
| WO | WO-2018/182221 A1 | 10/2018 |
| WO | WO-2018/183923 A1 | 10/2018 |
| WO | WO-2018/186365 A1 | 10/2018 |
| WO | WO-2018/195450 A1 | 10/2018 |
| WO | WO-2018/204176 A1 | 11/2018 |
| WO | WO-2018/204765 A1 | 11/2018 |
| WO | WO-2019/018562 A1 | 1/2019 |
| WO | WO-2019/028456 A1 | 2/2019 |
| WO | WO-2019/046668 A1 | 3/2019 |
| WO | WO-2019/055825 A1 | 3/2019 |
| WO | WO-2019/071325 A1 | 4/2019 |
| WO | WO-2019/079596 A1 | 4/2019 |
| WO | WO-2019/079607 A1 | 4/2019 |
| WO | WO-2019/089940 A1 | 5/2019 |
| WO | WO-2019/117179 A1 | 6/2019 |
| WO | WO-2019/121392 A1 | 6/2019 |
| WO | WO-2019/144126 A1 | 7/2019 |
| WO | WO-2019/228404 A1 | 12/2019 |
| WO | WO-2019/238786 A1 | 12/2019 |
| WO | WO-2019/246343 A1 | 12/2019 |
| WO | WO-2020/015744 A1 | 1/2020 |
| WO | WO-2020/018848 A1 | 1/2020 |
| WO | WO-2020/033960 A1 | 2/2020 |
| WO | WO-2020/061476 A1 | 3/2020 |
| WO | WO-2020/079569 A1 | 4/2020 |
| WO | WO-2020/079570 A1 | 4/2020 |
| WO | WO-2020/094156 A1 | 5/2020 |
| WO | WO-2020/156285 A1 | 8/2020 |
| WO | WO-2020/176597 A1 | 9/2020 |
| WO | WO-2020/177729 A1 | 9/2020 |
| WO | WO-2020/227437 A1 | 11/2020 |
| WO | WO-2020/255156 A1 | 12/2020 |
| WO | WO-2022/010150 A1 | 1/2022 |
| WO | WO-2022/187203 A1 | 9/2022 |

OTHER PUBLICATIONS

International Search Report and Written Opinion for Application No. PCT/US2022/018283, dated Jun. 3, 2022, 12 pages.
International Search Report and Written Opinion for Application No. PCT/US2022/039385, dated Oct. 21, 2022, 9 pages.

(56) References Cited

OTHER PUBLICATIONS

International Search Report and Written Opinion for Application No. PCT/CN2022/129034, dated Feb. 13, 2023, 18 pages.

\* cited by examiner

PPARG INVERSE AGONISTS AND USES THEREOF

RELATED APPLICATIONS

This application is a continuation of international patent application No. PCT/CN2022/129034, filed Nov. 1, 2022, which claims the benefit of priority to U.S. Provisional Application No. 63/274,596, filed Nov. 2, 2021 and U.S. Provisional Application No. 63/347,671, filed Jun. 1, 2022. The entire contents of each of h aforementioned application are which are incorporated in their entirety herein by reference.

BACKGROUND

PPARgamma (PPARG) is a type II ligand-dependent nuclear hormone receptor (belonging to the PPAR nuclear receptor subfamily) that functions as an obligate heterodimer with retinoid X receptors (RXRs). PPARG is predominantly expressed in adipose tissue, colon, macrophages and the luminal layers of the urothelium. PPARG is known as a master regulator of adipogenesis, functioning to regulate adipocyte differentiation, fatty acid storage and glucose metabolism. PPARG has also been shown to play an important role in the metabolism and inflammation of macrophages, where it is induced by IL4 and controls glutamine metabolism. In the normal urothelium, PPARG is critical for its homeostasis and regeneration.

The role for PPARG in cancer was originally inferred from genomic studies that identified a PAX8-PPARG chromosomal rearrangement in follicular thyroid carcinomas. More recently, PPARG has been found to be over-expressed and genetically altered in the luminal subtype of urothelial cancer. This is consistent with reports that long-term use of PPARG agonists is associated with an increased incidence of urothelial cancer. Most urothelial cancers are urothelial carcinoma, which are classified as either non-muscle-invasive urothelial cancer (NMIUC, 70%), muscle-invasive urothelial cancer (MIUC, 25%) or metastatic urothelial cancer (MUC, 5%). MIUC is usually diagnosed de novo but may arise from the 10 to 20% of NMIUC cases that eventually progress. MIUC is a heterogeneous and aggressive disease, associated with a five-year survival rate of 60% for patients with localized disease and less than 10% for patients with distant metastases. Molecular understanding of NMIUC and MIUC has improved significantly, including the association between molecular subtypes and urothelial differentiation. Several molecular classes of MIUC have been proposed, whereby an activated PPARG signature features prominently in the luminal subtypes. First-line treatment is chemotherapy with several options in chemo-ineligible or second line, but treatment options are limited with poor overall survival rates.

The need exists to develop effective PPARG modulators for treating cancers such as NMIUC, MIUC, and MUC, and related conditions.

SUMMARY

Provided herein are compounds having the Formula I:

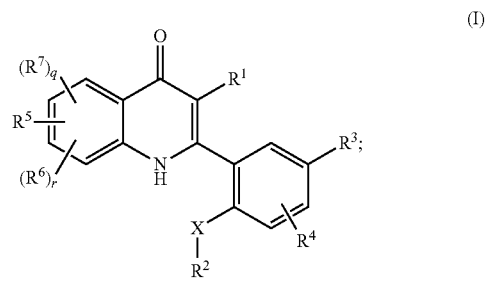

(I)

and pharmaceutically acceptable salts and compositions thereof, wherein $R^1$, $R^2$, $R^3$, $R^4$, $R^5$, $R^6$, $R^7$, X, q and r are as described herein. In one aspect, the disclosed compounds of Formula I and pharmaceutically acceptable salts thereof modulate PPARG (e.g., as agonists such as inverse agonists, and are useful in a variety of therapeutic applications such as, for example, in treating cancer. As such, their uses for treating diseases responsive to the inhibition of PPARG are included.

Pharmaceutical compositions comprising the compounds and pharmaceutically acceptable salts of the disclosed compounds of Formula I, as well as methods for their preparation are also included.

DETAILED DESCRIPTION

1. General Description of Compounds

Figure 1:
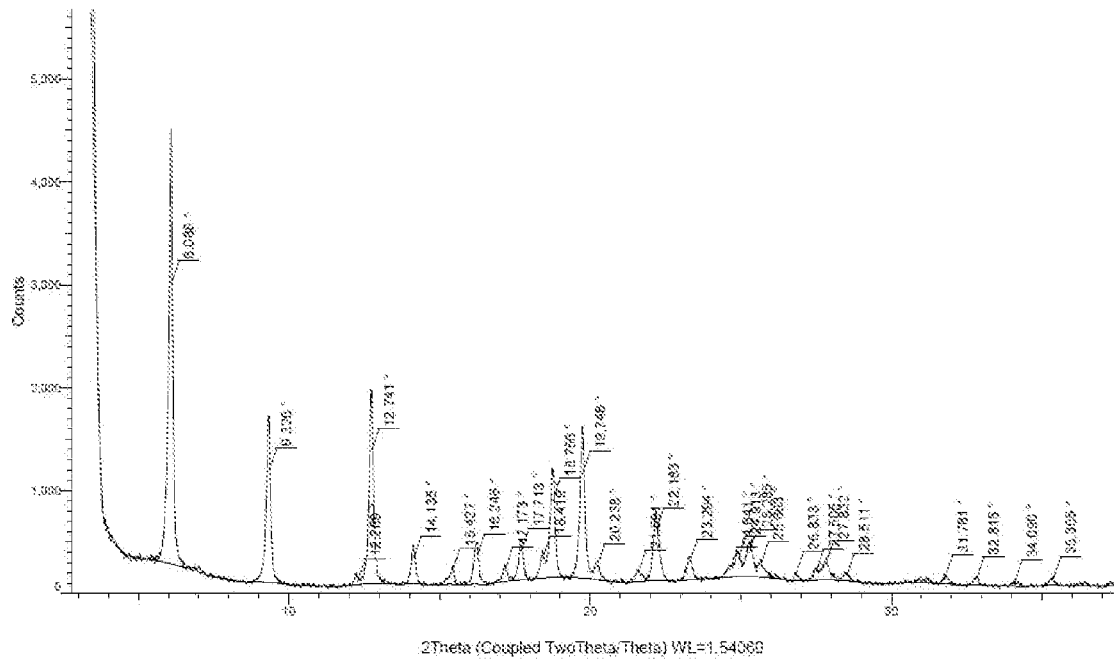
FIG. 1 depicts an X-ray powder diffraction pattern (XRPD) for crystalline Form A of 3-(5,7-difluoro-4-oxo-1,4-dihydroquinolin-2-yl)-4-(methylsulfonyl)benzonitrile.

In a first embodiment, provided herein is a compound of Formula I:

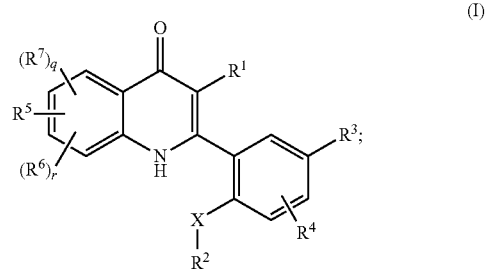

(I)

or a pharmaceutically acceptable salt thereof, wherein:
$R^1$ is hydrogen, halo, $(C_1-C_4)$alkyl, or hydroxyl;
X is S, SO, $SO_2$, or —SONH;
$R^2$ is $(C_1-C_4)$alkyl, $(C_1-C_4)$alkoxy, or halo$(C_1-C_4)$alkyl;
$R^3$ is cyano or nitro;
$R^4$ is hydrogen, halo, $(C_1-C_4)$alkyl, $(C_1-C_4)$alkoxy, or hydroxyl;

$R^5$ is halo, halo($C_1$-$C_4$)alkyl, or cyano;

$R^6$ is halo, halo($C_1$-$C_4$)alkyl, ($C_1$-$C_4$)alkyl, or cyano;

$R^7$ is halo, ($C_1$-$C_4$)alkyl, ($C_1$-$C_4$alkoxy, halo($C_1$-$C_4$)alkyl, halo($C_1$-$C_4$)alkoxy, —($C_1$-$C_4$)alkylOR$^a$, —($C_1$-$C_4$)alkylC(O)R$^a$, —($C_1$-$C_4$)alkylC(O)OR$^a$, —C(O)NR$^a$R$^b$, —($C_1$-$C_4$)alkylC(O)NR$^a$R$^b$, —C(O)R$^a$, —C(O)OR$^a$, —NR$^a$R$^b$, —($C_1$-$C_4$)alkylNR$^a$R$^b$, —C(O)NR$^a$SO$_3$H, —NR$^a$C(O)R$^b$, —NR$^a$C(O)OR$^b$, —NR$^a$C(S)OR$^b$, —NR$^c$C(O)N$^a$R$^b$, —NR$^c$C(S)NR$^a$R$^b$, —NR$^c$S(O)$_2$NR$^a$R$^b$, —C(S)R$^a$, —S(O)$_2$R$^a$, —S(O)R$^a$, —C(S)OR$^a$, —C(S)NR$^a$R$^b$, —NR$^a$C(S)R$^b$, —SR$^a$, phenyl, 4- to 6-membered heterocyclyl, and 5- to 7-membered heteroaryl, wherein each of said phenyl, 4- to 6-membered heterocyclyl, and 5- to 7-membered heteroaryl are optionally and independently substituted with 1 to 3 groups selected from $R^8$;

$R^8$ is selected from halo, ($C_1$-$C_4$)alkyl, halo($C_1$-$C_4$)alkyl, ($C_1$-$C_4$)alkoxy, halo($C_1$-$C_4$)alkoxy, nitro, oxo, cyano. —($C_1$-$C_4$)alkylOR$^d$, —($C_1$-$C_4$)alkylC(O)R$^d$, —($C_1$-$C_4$)alkylC(O)OR$^d$, —C(O)NR$^d$R$^e$, —($C_1$-$C_4$)alkylC(O)NR$^d$R$^e$, —C(O)R$^d$, —C(O)OR$^d$, —NR$^d$R$^e$, —($C_1$-$C_4$)alkylNR$^d$R$^e$, —C(O)NR$^d$SO$_3$H, —NR$^d$C(O)R$^e$, —NR$^d$C(O)OR$^e$, —NR$^d$C(S)OR$^e$, —NR$^f$C(O)N$^d$R$^e$, —NR$^f$C(S)NR$^d$R$^e$, —NR$^f$S(O)$_2$NR$^d$R$^e$, —C(S)R$^d$, —S(O)$_2$R$^d$, —S(O)R$^d$, —C(S)OR$^d$, —C(S)NR$^d$R$^e$, —NR$^d$C(S)R$^e$, and —SR$^d$;

$R^a$, $R^b$, $R^c$, $R^d$, $R^e$, and $R^f$ are each independently hydrogen or ($C_1$-$C_4$)alkyl; and q and r are each independently 0 or 1.

2. Definitions

When used in connection to describe a chemical group that may have multiple points of attachment, a hyphen (-) designates the point of attachment of that group to the variable to which it is defined. For example, —NR$^b$C(O)OR$^c$ and —NR$^b$C(S)OR$^c$ mean that the point of attachment for this group occurs on the nitrogen atom.

The terms "halo" and "halogen" refer to an atom selected from fluorine (fluoro, —F), chlorine (chloro, —Cl), bromine (bromo, —Br), and iodine (iodo, —I).

The term "alkyl" when used alone or as part of a larger moiety, such as "haloalkyl", and the like, means saturated straight-chain or branched monovalent hydrocarbon radical.

"Alkoxy" means an alkyl radical attached through an oxygen linking atom, represented by —O-alkyl. For example, "($C_1$-$C_4$)alkoxy" includes methoxy, ethoxy, proproxy, and butoxy.

The term "haloalkyl" includes mono, poly, and perhaloalkyl groups where the halogens are independently selected from fluorine, chlorine, bromine, and iodine.

"Haloalkoxy" is a haloalkyl group which is attached to another moiety via an oxygen atom such as, e.g., —OCHF$_2$ or —OCF$_3$.

The term oxo means the group =O.

The term "5- to 7-membered heteroaryl" used alone or as part of a larger moiety refers to a 5- to 7-membered aromatic radical containing 1-4 heteroatoms selected from N, O, and S. Monocyclic heteroaryl includes, for example, thienyl, furanyl, pyrrolyl, imidazolyl, pyrazolyl, triazolyl, tetrazolyl, oxazolyl, isoxazolyl, triazinyl, tetrazinyl, oxadiazolyl, thiazolyl, isothiazolyl, thiadiazolyl, pyridyl, pyridazinyl, pyrimidinyl, pyrazinyl, etc. Optional substituents on a heteroaryl group may be present on any substitutable position and, include. e.g., the position at which the heteroaryl is attached.

The term "4- to 6-membered heterocyclyl" means a 4- to 6-membered saturated or partially unsaturated heterocyclic ring containing 1 to 4 heteroatoms independently selected from N, O, and S. A heterocyclyl ring can be attached to its pendant group at any heteroatom or carbon atom that results in a stable structure. Examples of monocyclic saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, oxetanyl, dioxolanyl, morpholinyl, dihydrofuranyl, dihydropyranyl, dihydropyridinyl, tetrahydropyridinyl, dihydropyrimidinyl, and tetrahydropyrimidinyl. Optional substituents on a heterocyclyl group may be present on any substitutable position and, include. e.g., the position at which the heterocyclyl is attached.

The disclosed compounds may exist in one or more tautomeric forms, such as those below, and are included herein.

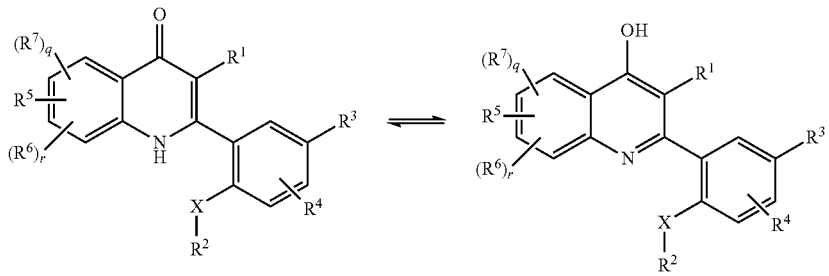

As used herein, "crystalline" refers to a solid form of a compound wherein there exists long-range atomic order in the positions of the atoms. The crystalline nature of a solid can be confirmed, for example, by examination of the X-ray powder diffraction pattern.

Unless otherwise specified, crystalline Form A of 3-(5,7-difluoro-4-oxo-1,4-dihydroquinolin-2-yl)-4-(methylsulfonyl)benzonitrile is a single crystalline form, meaning that 3-(5,7-difluoro-4-oxo-1,4-dihydroquinolin-2-yl)-4-(methylsulfonyl)benzonitrile is present as a single crystal or a plurality of crystals in which each crystal has the same crystal form (i.e., Form A).

The 2-theta values of the X-ray powder diffraction patterns for the crystalline form described herein may vary slightly from one instrument to another and also depending on variations in sample preparation and batch to batch variation due to factors such as temperature variation, sample displacement, and the presence or absence of an internal standard. Therefore, unless otherwise defined, the XRPD patterns/assignments recited herein are not to be construed as absolute and can vary ±0.2 degrees. It is well known in the art that this variability will account for the above factors without hindering the unequivocal identification of a crystal form. Unless otherwise specified, the 2-theta values provided herein were obtained using Cu Kα1 radiation.

Temperature values, e.g., for DSC peaks herein may vary slightly from one instrument to another and also depending on variations in sample preparation, batch to batch variation, and environmental factors. Therefore, unless otherwise defined, temperature values recited herein are not to be construed as absolute and can vary ±5 degrees or ±2 degrees.

"Substantially the same XRPD pattern" or "an X-ray powder diffraction pattern substantially similar to" a defined figure means that for comparison purposes, at least 90% of the peaks shown are present. It is to be further understood that for comparison purposes some variability in peak intensities from those shown are allowed, such as ±0.2 degrees.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

The term "effective amount" or "therapeutically effective amount" refers to an amount of a compound described herein that will elicit a desired or beneficial biological or medical response of a subject e.g., a dosage of between 0.01-100 mg/kg body weight/day.

3. Compounds

In a second embodiment, the compound of Formula I is of the Formula II:

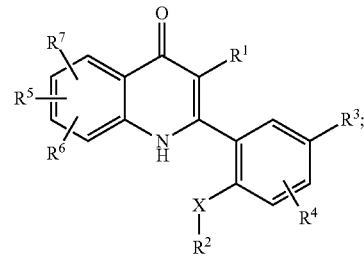

or a pharmaceutically acceptable salt thereof, wherein the variables are as described above for Formula I. Alternatively, as part of a second embodiment, the compound of Formula I is of the Formula II$^a$:

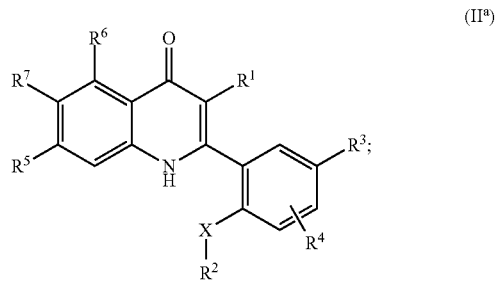

(II$^a$)

or a pharmaceutically acceptable salt thereof, wherein the variables are as described above for Formula I. In another alternative, as part of a second embodiment, the compound of Formula I is of the Formula III:

(III)

[Structure of Formula III: quinolin-4(1H)-one with R¹ at 3-position, R⁵ and R⁶ on benzo ring, 2-aryl group bearing R³, R⁴, and X–R²]

or a pharmaceutically acceptable salt thereof, wherein the variables are as described above for Formula I. In another alternative, as part of a second embodiment, the compound of Formula I is of the Formula III$^a$:

(III$^a$)

[Structure of Formula III$^a$: quinolin-4(1H)-one with R⁶ at 5-position, R⁵ at 7-position, R¹ at 3-position; 2-aryl group with R³, R⁴, X–R²]

or a pharmaceutically acceptable salt thereof, wherein the variables are as described above for Formula I. In another alternative, as part of a second embodiment, the compound of Formula I is of the Formula IV:

(IV)

[Structure of Formula IV: quinolin-4(1H)-one with R⁵, R¹, and 2-aryl substituted with R³, R⁴, X–R²]

or a pharmaceutically acceptable salt thereof, wherein the variables are as described above for Formula I. In another alternative, as part of a second embodiment, the compound of Formula I is of the Formula IV$^a$:

(IV$^a$)

[Structure of Formula IV$^a$: quinolin-4(1H)-one with R⁵ at 7-position, R¹ at 3-position; 2-aryl group with R³, R⁴, X–R²]

or a pharmaceutically acceptable salt thereof, wherein the variables are as described above for Formula I.

In a third embodiment, $R^1$ in the compound of Formula I or II, or a pharmaceutically acceptable salt thereof is hydrogen, wherein the remaining variables are as described above for Formula I.

In a fourth embodiment, $R^3$ in the compound of Formula I or II, or a pharmaceutically acceptable salt thereof is cyano, wherein the remaining variables are as described above for Formula I or the third embodiment.

In a fifth embodiment, $R^4$ in the compound of Formula I or II, or a pharmaceutically acceptable salt thereof is hydrogen, wherein the remaining variables are as described above for Formula I or any one of the third or fourth embodiments.

In a sixth embodiment, $R^5$ in the compound of Formula I or II, or a pharmaceutically acceptable salt thereof is halo or cyano, wherein the remaining variables are as described above for Formula I or any one of the third, fourth, or fifth embodiments. Alternatively, as part of a sixth embodiment, $R^5$ in the compound of Formula I or II, or a pharmaceutically acceptable salt thereof is halo, wherein the remaining variables are as described above for Formula I or any one of the third, fourth, or fifth embodiments. In another alternative, as part of a sixth embodiment, $R^5$ in the compound of Formula I or II, or a pharmaceutically acceptable salt thereof is chloro or fluoro, wherein the remaining variables are as described above for Formula I or any one of the third, fourth, or fifth embodiments. In another alternative, as part of a sixth embodiment, $R^5$ in the compound of Formula I or II, or a pharmaceutically acceptable salt thereof is fluoro, wherein the remaining variables are as described above for Formula I or any one of the third, fourth, or fifth embodiments.

In a seventh embodiment, $R^6$ in the compound of Formula I or II, or a pharmaceutically acceptable salt thereof is halo, wherein the remaining variables are as described above for Formula I or any one of the third to sixth embodiments. Alternatively, as part of a seventh embodiment, $R^6$ in the compound of Formula I or II, or a pharmaceutically acceptable salt thereof is fluoro or chloro, wherein the remaining variables are as described above for Formula I or any one of the third to sixth embodiments. In another alternative, as part of a seventh embodiment, $R^6$ in the compound of Formula I or II, or a pharmaceutically acceptable salt thereof is fluoro, wherein the remaining variables are as described above for Formula I or any one of the third to sixth embodiments.

In an eighth embodiment, $R^7$ in the compound of Formula I or II, or a pharmaceutically acceptable salt thereof is halo, halo($C_1$-$C_4$)alkyl, ($C_1$-$C_4$)alkyl, ($C_1$-$C_4$)alkoxy, —($C_1$-$C_4$)alkylOR$^a$, —C(O)NR$^a$R$^b$, phenyl, 4- to 6-membered heterocyclyl, and 5- to 7-membered heteroaryl, wherein each of said phenyl, 4- to 6-membered heterocyclyl, and 5- to 7-membered heteroaryl are optionally and independently substituted with 1 to 3 groups selected from $R^8$, wherein the remaining variables are as described above for Formula I or any one of the third to seventh embodiments. Alternatively, as part of an eighth embodiment, R in the compound of Formula I or II, or a pharmaceutically acceptable salt thereof is halo, halo($C_1$-$C_4$)alkyl, ($C_1$-$C_4$)alkyl, ($C_1$-$C_4$)alkoxy, —($C_1$-$C_4$)alkylOR$^a$, —C(O)NR$^a$R$^b$, phenyl pyridinyl, piperazinyl, piperidinyl, pyrrolidinyl, thiomorpholinyl, pyrazolyl, and oxetanyl, wherein each of said phenyl, pyridinyl, pyrazolyl, pyrrolidinyl, piperazinyl, thiomorpholinyl, piperidinyl, and oxetanyl are optionally and independently substituted with 1 to 3 groups selected from $R^8$, wherein the remaining variables are as described above for Formula I or any one of the third to seventh embodiments. In another alternative, as part of an eighth embodiment, $R^7$ in the compound of Formula I or II, or a pharmaceutically acceptable salt thereof is halo, halo($C_1$-$C_4$)alkyl, ($C_1$-$C_4$)alkyl, ($C_1$-$C_4$)alkoxy, —($C_1$-$C_4$)alkylOR$^a$, —C(O)NR$^a$R$^b$, phenyl, pyridinyl, pyrazolyl, and oxetanyl, wherein each of said phenyl, pyridinyl, pyrazolyl, and oxetanyl are optionally and independently substituted with 1 to 3 groups selected from R$^8$, wherein the remaining variables are as described above for Formula I or any one of the third to seventh embodiments. In another alternative, as part of an eighth embodiment, R$^7$ in the compound of Formula I or II, or a pharmaceutically acceptable salt thereof is pyrazolyl, pyridinyl, or piperazinyl, each of which optionally and independently substituted with 1 to 3 groups selected from R$^8$, wherein the remaining variables are as described above for Formula I or any one of the third to seventh embodiments. In yet another alternative, as part of an eighth embodiment, R$^7$ in the compound of Formula I or II, or a pharmaceutically acceptable salt thereof is pyrazolyl optionally and independently substituted with 1 to 3 groups selected from R$^8$, wherein the remaining variables are as described above for Formula I or any one of the third to seventh embodiments.

In a ninth embodiment, R$^8$ in the compound of Formula I or II, or a pharmaceutically acceptable salt thereof is selected from halo, ($C_1$-$C_4$)alkyl, halo($C_1$-$C_4$)alkyl, ($C_1$-$C_4$)alkoxy, halo($C_1$-$C_4$)alkoxy, oxo, and cyano, wherein the remaining variables are as described above for Formula I or any one of the third to eighth embodiments. Alternatively, as part of an ninth embodiment. R$^8$ in the compound of Formula I or II, or a pharmaceutically acceptable salt thereof is halo($C_1$-$C_4$)alkyl, wherein the remaining variables are as described above for Formula I or any one of the third to eighth embodiments. In another alternative, as part of an ninth embodiment, R$^8$ in the compound of Formula I or II, or a pharmaceutically acceptable salt thereof is ($C_1$-$C_4$) alkyl, wherein the remaining variables are as described above for Formula I or any one of the third to eighth embodiments.

In a tenth embodiment, R$^2$ in the compound of Formula I or II, or a pharmaceutically acceptable salt thereof is halo ($C_1$-$C_4$)alkyl or ($C_1$-$C_4$)alkyl, wherein the remaining variables are as described above for Formula I or any one of the third to ninth embodiments. Alternatively, as part of a tenth embodiment, R$^2$ in the compound of Formula I or II, or a pharmaceutically acceptable salt thereof is ($C_1$-$C_4$)alkyl, wherein the remaining variables are as described above for Formula I or any one of the third to ninth embodiments. In another alternative, as part of a tenth embodiment, R$^2$ in the compound of Formula I or II, or a pharmaceutically acceptable salt thereof is $CH_3$, $CH_2CH_3$, $CF_3CH_2$, $CF_3$, $CH(CH_3)_2$, or $CH_2CH(CH_3)_2$, wherein the remaining variables are as described above for Formula I or any one of the third to ninth embodiments. In another alternative, as part of a tenth embodiment, R$^2$ in the compound of Formula I or II, or a pharmaceutically acceptable salt thereof is $CH_3$, wherein the remaining variables are as described above for Formula I or any one of the third to ninth embodiments.

In an eleventh embodiment, X in the compound of Formula I or II, or a pharmaceutically acceptable salt thereof is $SO_2$, wherein the remaining variables are as described above for Formula I or any one of the third to tenth embodiments.

Compounds having the Formula I and H are further disclosed in the Exemplification and are included in the present disclosure. Pharmaceutically acceptable salts thereof as well as the neutral forms are included. In certain aspects, one or more hydrogen atoms on a compound disclosed herein may be replaced by deuterium.

4. Crystalline Form

Also provided herein is crystalline Form A of 3-(5,7-difluoro-4-oxo-1,4-dihydroquinolin-2-yl)-4-(methylsulfonyl)benzonitrile. Also provided herein are pharmaceutical compositions comprising crystalline Form A of 3-(5,7-difluoro-4-oxo-1,4-dihydroquinolin-2-yl)-4-(methylsulfonyl) benzonitrile. Further provided is the use of crystalline Form A of 3-(5,7-difluoro-4-oxo-1,4-dihydroquinolin-2-yl)-4-(methylsulfonyl)benzonitrile for treating diseases responsive to the inhibition of PPARG.

In one aspect, provided herein is crystalline Form A of 3-(5,7-difluoro-4-oxo-1,4-dihydroquinolin-2-yl)-4-(methylsulfonyl)benzonitrile, wherein the crystalline form is characterized by at least three x-ray powder diffraction peaks at 2θ angles selected from 6.1°, 9.3°, 12.7°, 18.8°, and 19.8°. Alternatively, crystalline Form A of 3-(5,7-difluoro-4-oxo-1,4-dihydroquinolin-2-yl)-4-(methylsulfonyl)benzonitrile is characterized by at least four x-ray powder diffraction peaks at 2Θ angles selected from 6.1°, 9.3°, 12.7°, 18.8°, and 19.8°. In another alternative, crystalline Form A of 3-(5,7-difluoro-4-oxo-1,4-dihydroquinolin-2-yl)-4-(methylsulfonyl)benzonitrile is characterized by x-ray powder diffraction peaks at 2θ angles selected from 6.10, 9.3°, 12.7°, 18.80, and 19.8°. In yet another alternative, crystalline Form A of 3-(5,7-difluoro-4-oxo-1,4-dihydroquinolin-2-yl)-4-(methylsulfonyl)benzonitrile is characterized by x-ray powder diffraction peaks at 2Θ angles selected from 6.1°. 9.3°, and 12.7°. In yet another alternative, crystalline Form A of 3-(5,7-difluoro-4-oxo-1,4-dihydroquinolin-2-yl)-4-(methylsulfonyl)benzonitrile is characterized by x-ray powder diffraction peaks at 2Θ angles selected from 6.1°, 9.3°, 12.7°, and 19.8°. In yet another alternative, crystalline Form A of 3-(5,7-difluoro-4-oxo-1,4-dihydroquinolin-2-yl)-4-(methylsulfonyl)benzonitrile is characterized by at least three x-ray powder diffraction peaks at 2θ angles selected from 6.1°, 9.3°, 12.7°, 17.7°, 18.8°. 19.8°, and 22.2°. In yet another alternative, crystalline Form A of 3-(5,7-difluoro-4-oxo-1, 4-dihydroquinolin-2-yl)-4-(methylsulfonyl)benzonitrile is characterized by at least four x-ray powder diffraction peaks at 2θ angles selected from 6.1°, 9.3°, 12.7°, 17.7°, 18.8°, 19.8°, and 22.2°. In yet another alternative, crystalline Form A of 3-(5,7-difluoro-4-oxo-1,4-dihydroquinolin-2-yl)-4-(methylsulfonyl)benzonitrile is characterized by at least five x-ray powder diffraction peaks at 2θ angles selected from 6.1°, 9.3°, 12.7°, 17.7°, 18.8°, 19.8°, and 22.2°. In yet another alternative, crystalline Form A of 3-(5,7-difluoro-4-oxo-1,4-dihydroquinolin-2-yl)-4-(methylsulfonyl)benzonitrile is characterized by at least six x-ray powder diffraction peaks at 2θ angles selected from 6.1°, 9.3°, 12.7°. 17.7°, 18.8°, 19.8°, and 22.2°. In yet another alternative, crystalline Form A of 3-(5,7-difluoro-4-oxo-1,4-dihydroquinolin-2-yl)-4-(methylsulfonyl)benzonitrile is characterized by x-ray powder diffraction peaks at 2θ angles selected from 6.1°, 9.3°, 12.7°, 17.7°, 18.8°, 19.8°, and 22.2°. In yet another alternative, crystalline Form A of 3-(5,7-difluoro-4-oxo-1, 4-dihydroquinolin-2-yl)-4-(methylsulfonyl)benzonitrile is characterized by at least three, at least four, at least five, at least six, at least eight, at least nine, or at least 10 peaks selected from those in Table 1. In yet another alternative, crystalline Form A of 3-(5,7-difluoro-4-oxo-1,4-dihydroquinolin-2-yl)-4-(methylsulfonyl)benzonitrile is characterized by an XRPD substantially similar to FIG. 1. In yet another alternative, crystalline Form A of 3-(5,7-difluoro-4-oxo-1, 4-dihydroquinolin-2-yl)-4-(methylsulfonyl)benzonitrile is characterized by a Differential Scanning Calorimetry (DSC) with a endotherm at 304° C. (onset temperature), wherein the crystalline form may also comprise XRPD peaks at 2θ angles selected from any of those described above. In yet another alternative, crystalline Form A of 3-(5,7-difluoro-4-oxo-1,4-dihydroquinolin-2-yl)-4-(methylsulfonyl)benzonitrile is characterized by a Differential Scanning Calorimetry (DSC) substantially similar to FIG. 2, wherein the crystalline Form 1 may also comprise XRPD peaks at 2θ angles selected from any of those described above.

TABLE 1

| Position (2θ) | Relative Intensity (%) |
|---|---|
| 6.09 | 100.0 |
| 9.33 | 39.6 |
| 12.29 | 1.1 |
| 12.74 | 47.1 |
| 14.14 | 8.9 |
| 15.43 | 4.7 |
| 16.25 | 9.8 |
| 17.17 | 4.1 |
| 17.71 | 10.3 |
| 18.420 | 6.7 |
| 18.76 | 27.2 |
| 19.75 | 37.3 |
| 20.24 | 4.7 |
| 21.60 | 2.9 |
| 22.18 | 17.6 |
| 23.29 | 6.0 |
| 24.64 | 2.6 |
| 24.91 | 6.0 |
| 25.29 | 8.7 |
| 25.66 | 4.2 |
| 26.83 | 2.2 |
| 27.51 | 3.0 |
| 27.83 | 5.8 |
| 28.51 | 1.6 |
| 31.78 | 2.2 |
| 32.82 | 1.8 |
| 34.09 | 1.4 |
| 35.37 | 2.1 |

6. General Processes

In one aspect, as part of a twelfth embodiment, compounds of Formula I can be prepared by a process comprising: reacting a compound of Formula A:

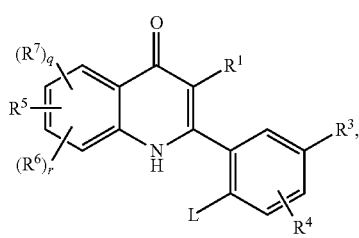

(A)

wherein L is a leaving group, and wherein the remaining variables are as described above for the compound of Formula I or any one of the third to ninth embodiments, with the corresponding sulfur nucleophile of $XR^2$ to form the compound of Formula I. In some aspects, the leaving group in the twelfth embodiment, is a halogen leaving group such as chloro. In some aspects, as part of a twelfth embodiment, the compound of Formula A is reacted with the sulfur nucleophile in the presence of a copper catalyst such as, e.g., a copper(I) catalyst (e.g. CuI) or copper(II) catalyst (e.g., $Cu_2O$, $Cu(OAc)_2$, CuBr, CuCl, and the like. In some aspects, as part of a twelfth embodiment, the compound of Formula A is reacted with the sulfur nucleophile in the presence of a copper ligand such as e.g., an organic base (e.g., proline, quinolone-8-ol, hydroxyproline, N-Me glylcine, and dimethyl glycine). In some aspects, q and r are each 0 in the twelfth embodiment. In some aspects, $XR^2$ in the twelfth embodiment is $—S(O)_2(C_1-C_4)$alkyl such as $—S(O)_2CH_3$. In some aspects, as part of a twelfth embodiment, the compound of Formula A is reacted with the sulfur nucleophile in the presence of an organic solvent such as polar aprotic solvent (e.g., DMSO, DMF, NMP and DMA). In some aspects, as part of a twelfth embodiment, the compound of Formula A is reacted with the sulfur nucleophile in the presence of a base such as $K_3PO_4$, $K_2CO_3$, $NaHCO_3$, $K_2HPO_4$, $Na_2CO_3$, $Na_3PO_4$, $Li_3PO_4$, KOtBu and KHMDS. In some aspects, the compound of Formula I in the twelfth embodiment is 3-(5,7-difluoro-4-oxo-1,4-dihydroquinolin-2-yl)-4-(methylsulfonyl)benzonitrile. In some aspects, the compound of Formula I in the twelfth embodiment is crystalline Form A 3-(5,7-difluoro-4-oxo-1,4-dihydroquinolin-2-yl)-4-(methylsulfonyl)benzonitrile as defined by one or more of the XRPD peaks defined herein.

In one aspect, as part of a thirteenth embodiment, provided is a process for preparing a compound having the Formula A:

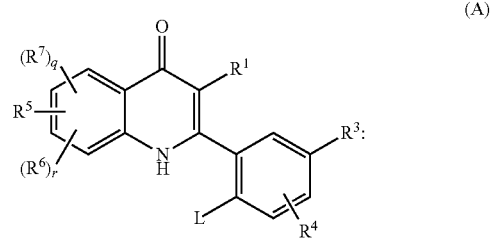

(A)

wherein L is a leaving group, and wherein the remaining variables are as described above for the compound of Formula I or any one of the third to ninth embodiments, said process comprising: reacting a compound having the Formula B:

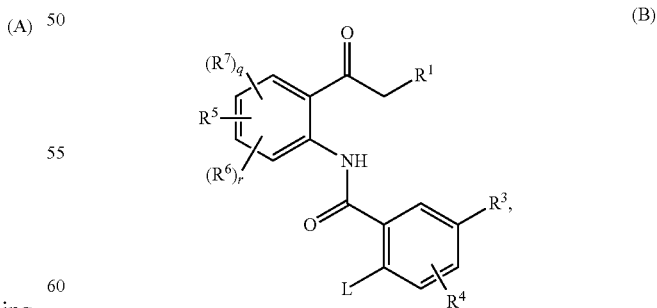

(B)

with a base. In some aspects, the base in the eleventh embodiment is an inorganic base such as LiOtBu, LiOH, NaOH, KOH and CsOH·$H_2O$. In some aspects, the compound having the Formula B the eleventh embodiment is reacted with the base in the presence of an organic solvent such as a polar aprotic solvent like THF, 2-MeTHF, CPME, dioxane, and NMP. In some aspects, the base in the eleventh embodiment is LiOtBu. In some aspects, the leaving group in the thirteenth embodiment is a halogen leaving group such as chloro. In some aspects, q and r are each 0 in the thirteenth embodiment. In some aspects, the compound of Formula A in the thirteenth embodiment, is

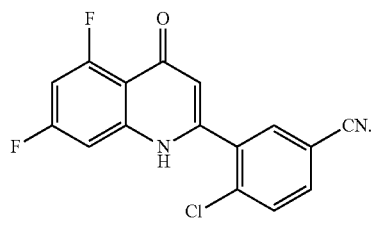 [SMILES: N#Cc1ccc(Cl)c(-c2cc(=O)c3c(F)cc(F)cc3[nH]2)c1]

In some aspects, the compound of Formula B in the thirteenth embodiment, is

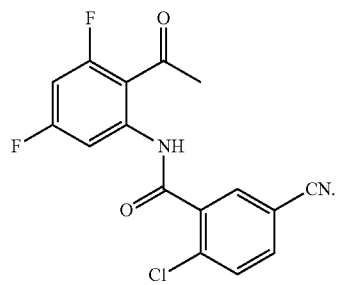 [SMILES: CC(=O)c1c(F)cc(F)cc1NC(=O)c1cc(C#N)ccc1Cl]

In one aspect, as part of a fourteenth embodiment, provided is a process for preparing a compound having the Formula B:

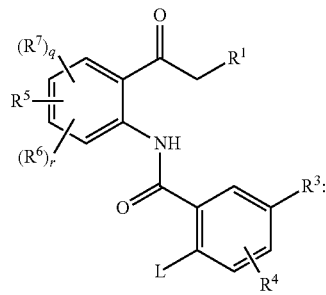

(B)

wherein L is a leaving group such as a halogen leaving group (e.g., chloro), and wherein the remaining variables are as described above for the compound of Formula I or any one of the third to ninth embodiments, said process comprising: reacting a compound having the Formula C:

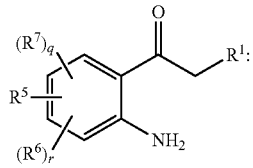

(C)

with a compound having the Formula D:

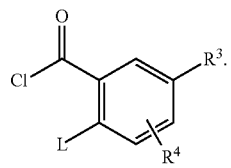

(D)

In some aspects, q and r are each 0 in the fourteenth embodiment. In some aspects, the compound of Formula B in the fourteenth embodiment, is

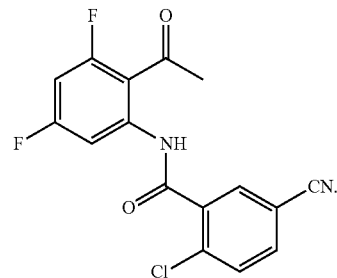 [SMILES: CC(=O)c1c(F)cc(F)cc1NC(=O)c1cc(C#N)ccc1Cl]

In some aspects, the compound of Formula C in the fourteenth embodiment, is

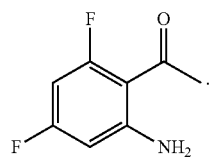

In some aspects, the compound of Formula D in the fourteenth embodiment, is

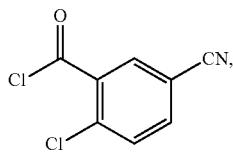

wherein L is as defined above.

In one aspect, as part of a fifteenth embodiment, provided is a process for preparing a compound having the Formula C:

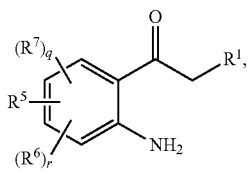

(C)

wherein the remaining variables are as described above for the compound of Formula I or any one of the third, sixth, seventh, or eighth embodiments, said process comprising reacting a compound having the Formula E:

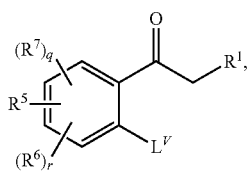

(E)

where $L^v$ is a leaving group such as e.g., a halogen (e.g., fluoro), with ammonia ion such as from ammonium hydroxide to form the compound having the Formula C. In some aspects, the compound having the Formula E is reacted with ammonia ion such as from ammonium hydroxide in the presence of an organic solvent such as a polar aprotic or polar protic solvent like THF, 2-MeTHF, IPA, toluene, acetonitrile, DMP, NMP, CPME and MTBE. In some aspects, the compound having the Formula E is reacted with ammonia ion such as from ammonium hydroxide in the presence of 2-MeTHF. In some aspects, q and r are each 0 in the fifteenth embodiment. In some aspects, the compound of Formula C in the fifteenth embodiment, is

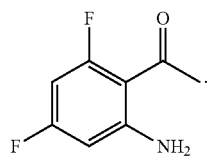

In some aspects, the compound of Formula E in the fifteenth embodiment, is

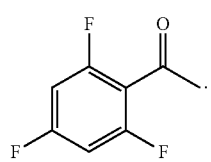

In one aspect, as part of a sixteenth embodiment, provided is a process for preparing a compound having the Formula D:

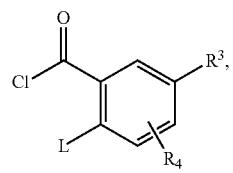

(D)

wherein L is a leaving group such as e.g., a halogen leaving group (e.g., chloro) and wherein the remaining variables are as described above for Formula I or any one of the fourth or fifth embodiments, said process comprising reacting a compound having the Formula F:

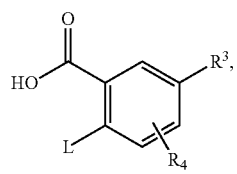

(F)

with a chlorinating agent such as e.g., thionyl chloride. In some aspects, the compound of Formula D in the sixteenth embodiment, is

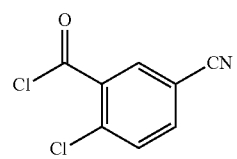 [SMILES: N#Cc1ccc(Cl)c(C(=O)Cl)c1]

In some aspects, the compound of Formula F in the sixteenth embodiment, is

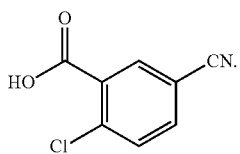 [SMILES: N#Cc1ccc(Cl)c(C(=O)O)c1]

In one aspect, as part of a seventeenth embodiment, provided is a process for preparing a compound having the Formula G:

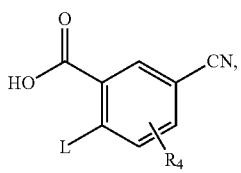

(G)

wherein L is a leaving group such as a halogen leaving group (e.g., chloro) and $R^4$ is as described above for Formula I or any one of the fourth or fifth embodiments, said process comprising reacting a compound having the Formula H:

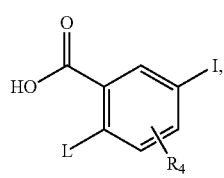

(H)

with a palladium catalyst such as e.g., Pd(OAc)$_2$, Pd$_2$(dba)$_3$. In some aspects, as part of a seventeenth embodiment, the process further comprises the addition of a palladium coupling ligand such as e.g., dppb, tBu$_3$HBF$_4$, dppp, Ph$_3$P, XantPhos, dppf, AmgenPHOS, DPEPhos, RuPHOS, R-BI-NAP, (o-tol)$_3$P, S-PHOS, X-Phos, tBu-XPhos, and Ph$_2$-CH$_2$CH$_2$-(2-Pyr)). Solvent: DMAc, tBuOH, DMAc/water, and tBuOH/water. In some aspects, the compound of Formula G in the seventeenth embodiment, is

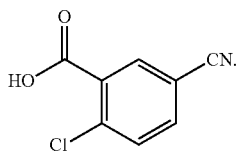

In some aspects, the compound of Formula H in the seventeenth embodiment, is

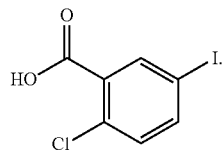

Other processes of preparation are disclosed in the exemplification section and are included as part of the present invention.

6. Uses, Formulation and Administration

The compounds and compositions described herein are generally useful for modulating the activity of PPARG. In some aspects, the compounds, pharmaceutical acceptable salts, and pharmaceutical compositions described herein inhibit the activity PPARG. In some aspects, the compounds and pharmaceutical acceptable salts disclosed herein are agonists of PPARG. In some aspects, the compounds and pharmaceutical acceptable salts disclosed herein are agonists of PPARG. In some aspects, the compounds and pharmaceutical acceptable salts disclosed herein are inverse agonists of PPARG. In one aspect, "inverse-agonists" refer to agents that bind to the same receptor binding site as a agonist (e.g., the binding site of a nuclear receptor such as PPARG) and not only antagonizes the effects of an agonist but, moreover, exerts the opposite effect by suppressing spontaneous receptor signaling (when present).

In some aspects, the compounds and pharmaceutical acceptable salts disclosed herein overcome the activated state of PPARG function resulting from alteration in PPARG activity (mutation, amplification or overexpression) or from RXRA activating mutations. In some aspect, the compounds and pharmaceutical acceptable salts disclosed herein increase the repressive state (NCOR1 recruitment) to a higher degree than previously disclosed PPARG modulators such as prior inverse agonists. Such results even arise in the mutant context. See e.g., the table qualitatively assessing NCOR1 recruitment and repression of PPARG target genes in HT1197 in the Exemplification section.

In some aspects, the compounds and pharmaceutical compositions described herein are useful in treating a disorder associated with PPARG function. Thus, provided herein are methods of treating a disorder associated with PPARG function, comprising administering to a subject in need thereof, a therapeutically effective amount of a compound described herein, or a pharmaceutically acceptable salt thereof, or a pharmaceutical composition comprising a disclosed compound or pharmaceutically acceptable salt thereof.

Also provided is the use of a compound described herein, or a pharmaceutically acceptable salt thereof, or a pharmaceutical composition comprising a disclosed compound or pharmaceutically acceptable salt thereof, for the manufacture of a medicament for treating a disorder associated with PPARG function. Also provided is a compound described herein, or a pharmaceutically acceptable salt thereof, or a pharmaceutical composition comprising a disclosed compound or pharmaceutically acceptable salt thereof, for use in treating a disorder associated with PPARG.

In one aspect, the disorder associated with PPARG is cancer. In some aspects, the cancer is associated with an up-regulated peroxisome proliferator-activated receptor (PPAR) signaling pathway. In some aspects, the up-regulated PPAR signaling pathway is associated with increased expression of one or more genes selected from Uroplakin 1A (UPK1A). Uroplakin IB (UPKTB). Uroplakin (UPK2), Keratin 20 (KRT20). GATA Binding Protein 3 (GAT A3), Nuclear Receptor Corepressor 1 (NCOR1), Nuclear Receptor Corepressor 2 (NCOR2), Fatty Acid Binding Protein 4 (FABP4), Forkhead Box A1 (FOXA1), CD36 Molecule (CD36), Acyl-CoA Oxidase 1 (ACOXI), 3-Hydroxy-3-Methylglutaryl-CoA Synthase 2 (HMGCS2), Acyl-CoA Synthetase Long-Chain Family Member 5 (ACSLS), Arachidonate 5-Lipoxygenase (ALOX5), Acyl-CoA Synthetase Long-Chain Family Member 1 (ACSL1), and Angiopoietin Like 4 (ANGPTL4).

In some aspects, the cancer treated by the compounds, pharmaceutically acceptable salt thereof, and pharmaceutical compositions described herein is selected from breast cancer, pancreatic cancer, ovarian cancer, prostate cancer, renal cancer, bladder cancer, testicular cancer, urothelial cancer (e.g., non-muscle-invasive urothelial cancer, muscle-invasive urothelial cancer, metastatic urothelial cancer), skin cancer, melanoma, colon cancer, kidney cancer, brain cancer and a hematopoietic cancer (e.g., lymphoma, multiple myeloma and leukemia). In one aspect, the cancer treated by the compounds, pharmaceutically acceptable salt thereof, and pharmaceutical compositions described herein is urothelial cancer such as non-muscle-invasive urothelial cancer, muscle-invasive urothelial cancer, and metastatic urothelial cancer.

Other uses besides cancer are contemplated and include e.g., metabolic diseases (e.g., osteoporosis, rachitis, arthrosis, obesity, type I and type II diabetes mellitus), lipid metabolism disorder, pancreatitis, glucose metabolism disorder, diabetic neuropathy, diabetic complications, hyperuricemia, osteoporosis, rachitis, arthrosis inflammatory diseases (e.g., inflammatory skin diseases such as psoriasis, atopic dermatitis, eczema, acne vulgaris, other dermatitides and pruritus), pulmonary disorders (e.g., asthma and chronic obstructive pulmonary disease), autoimmune disease, neurodegenerative disease (e.g., multiple sclerosis, ALzheimer's disease, and Parkinson's disease), cardiovascular diseases (e.g., selected from atherosclerosis, venous and arterial occlusive diseases), restenosis after invasive procedures, cardiomyopathy, myocardial fibrosis, congestive heart failure, angiogenesis and neovascularization in neoplastic diseases and renal diseases.

In certain aspects, a pharmaceutical composition described herein is formulated for administration to a patient in need of such composition. Pharmaceutical compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the pharmaceutical compositions described herein may be aqueous or oleaginous suspension. These suspensions may be formulated according to techniques known in the art using suitable dispersing or wetting agents and suspending agents.

In some aspects, the pharmaceutical compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the pharmaceutical composition.

EXEMPLIFICATION

Chemical Synthesis

The representative examples that follow are intended to help illustrate the present disclosure, and are not intended to, nor should they be construed to, limit the scope of the invention.

General starting materials used were obtained from commercial sources or prepared in other examples, unless otherwise noted.

DSC was performed using a Mettler Toledo DSC$^{3+}$. The sample (1-5 mg) was weighed directly in a 40 µL hermetic aluminum pan with a pinhole and analyzed according to the parameters below:

| Method | Ramp |
|---|---|
| Sample size | 3-5 mg |
| Heating rate | 10.0° C./min |
| Temperature range | 30 to 300° C. |
| Method gas | $N_2$ at 60.00 mL/min |

XRPD samples were analyzed using a Bruker D8 ADVANCE X-ray diffractometer using copper radiation (Cu Kα, λ=1.54060 Å). The generator was operated at a voltage of 40 KV and an amperage of 40 mA. Data were collected with a scanning range of 4 to 40° with a step size of 0.02°, scanning speed of 10°/minute and a sample rotation speed of 15 rpm.

Preparation of Compounds

The compounds claimed herein were prepared following the procedures outlined in the following schemes.

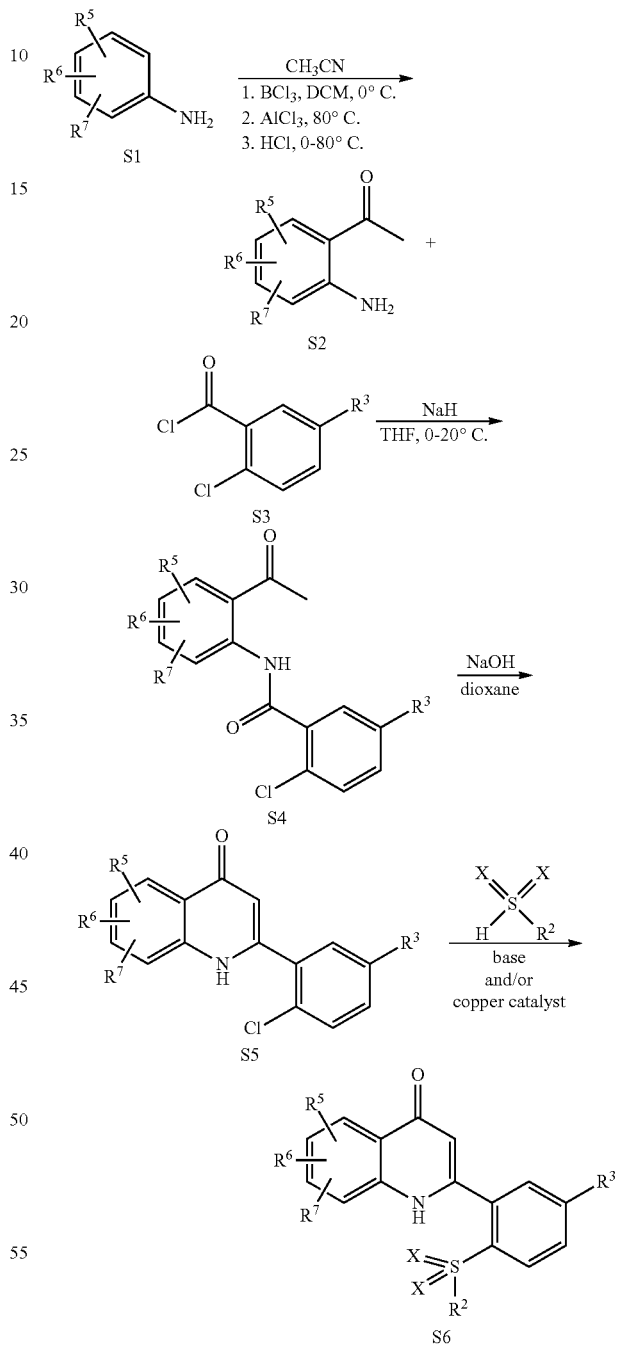

Quinolones like S6 may be prepared by the general synthetic methods shown in Scheme 1, Compounds of formula S2 may be prepared from the anilines S1 by treatment with acetonitrile, boron trichloride, aluminum trichloride and HCl in an organic solvent such as dichloromethane. Treatment of the acetylaniline S2 with an acyl chloride S3 yields intermediates of formula S4. Quinolones like S5 may then be prepared by treatment of S4 with a hydroxide base in an organic solvent such as dioxane at elevated temperature. The chloride on S5 may then be replaced with sulfur-based nucleophiles to provide S6, via an SNAr reaction or via a copper catalysis. Acyl chlorides S3 may be prepared from the corresponding acid by treatment with thionyl chloride or oxalyl chloride in an organic solvent such as dichloromethane.

Scheme 2.

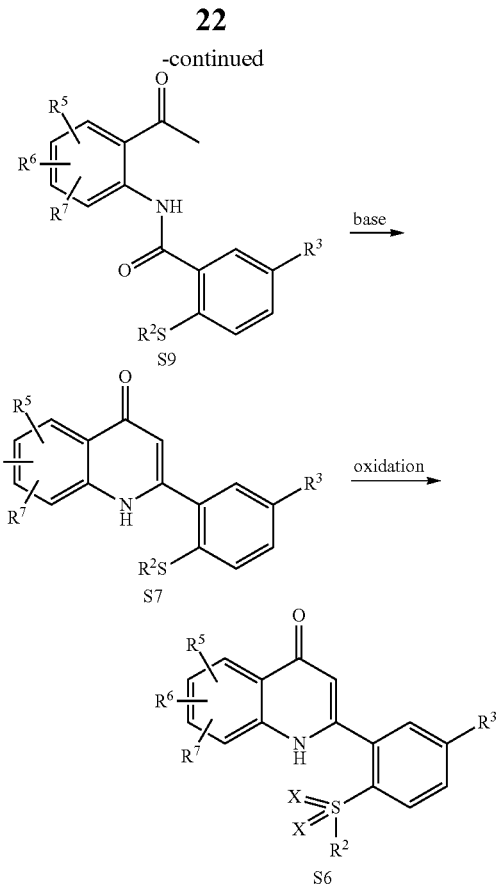

Certain quinolone analogues S6 may also be prepared via a two-step process consisting of nucleophile addition of a thiol to S5 followed by oxidation of the thioether S7.

Scheme 3.

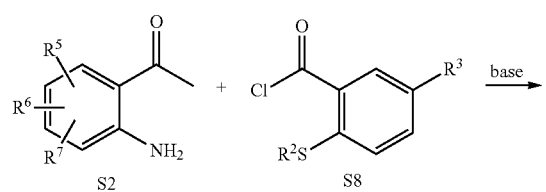

Certain quinolone analogues S6 may also be prepared a three-step process consisting of acylation of S2 with S8 to yield S9, cyclization amide S9 to yield quinolones S7, and oxidation of the thioether of S7.

Preparation of Starting Materials

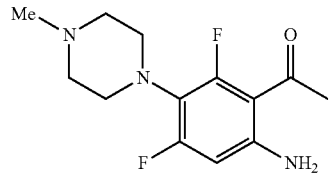 [SMILES: CC(=O)c1c(N)cc(F)c(N2CCN(C)CC2)c1F]

1-(6-amino-2,4-difluoro-3-(4-methylpiperazin-1-yl) phenyl)ethan-1-one

Step 1, 1-(3-bromo-2,6-difluoro-4-nitrophenyl)-4-methylpiperazine: To a solution 2-bromo-3,4,5-trifluoro-1-nitrobenzene (5 g, 19.5 mmol, 1.0 eq) in DMSO (50 mL) was added K₂CO₃ (4.05 g, 29.3 mmol, 1.5 eq) and 1-methylpiperazine (1.96 g, 19.5 mmol, 2.2 mL, 1.0 eq). The mixture was stirred at 20° C. for 16 hrs. LCMS showed compound 1 was consumed completely and one main peak with desired mass was detected. The suspension was filtered through a pad of Celite and the pad cake was washed with EtOAc (10 mL*3). The filtrate was extracted with EtOAc (20 mL*3) and H₂O (50 mL). The combined organic layers were washed with brine (15 mL), dried over anhydrous Na₂SO₄, filtered and concentrated under reduced pressure to give 1-(3-bromo-2,6-difluoro-4-nitrophenyl)-4-methylpiperazine (6.5 g, 99.0% yield) as a yellow solid. $^1$H NMR (400 MHz, CHLOROFORM-d) δ 7.66 (dd, J=1.8, 11.8 Hz, 1H), 3.40 (br t, J=4.8 Hz, 4H), 2.59-2.50 (m, 4H), 2.36 (s, 3H).

Step 2, 2-bromo-3,5-difluoro-4-(4-methylpiperazin-1-yl) aniline: To a solution of 1-(3-bromo-2,6-difluoro-4-nitrophenyl)-4-methylpiperazine (6.5 g, 19.3 mmol, 1.0 eq) in EtOH (40 mL) was added a solution of NH$_4$Cl (5.17 g, 96.7 mmol, 5.0 eq) in H$_2$O (20 mL) and Fe (5.40 g, 96.7 mmol, 5.0 eq). The mixture was stirred at 80° C. for 2 hrs. LCMS showed compound 2 was consumed completely and one main peak with desired mass was detected. The suspension was filtered through a pad of Celite and the pad cake was washed with EtOAc (50 mL*3). The reaction mixture was concentrated under reduced pressure to remove solvent. The residue was extracted with EtOAc (10 mL*3) and H$_2$O (10 mL). The combined organic layers were washed with brine (5 mL), dried over anhydrous Na$_2$SO$_4$, filtered and concentrated under reduced pressure to give 2-bromo-3,5-difluoro-4-(4-methylpiperazin-1-yl)aniline (4.5 g, 76.0% yield) as a yellow solid. $^1$H NMR (400 MHz, CHLOROFORM-d) δ 6.27 (br s, 2H), 6.11 (dd, J=1.8, 12.8 Hz, 1H), 3.17-3.01 (m, 4H), 2.57 (d, J=8.8 Hz, 3H), 2.35 (s, 3H), 2.30-2.30 (m, 1H), 1.41-1.16 (m, 3H).

Step 3, 1-(6-amino-2,4-difluoro-3-(4-methylpiperazin-1-yl)phenyl)ethan-1-one: To a solution of tributyl(1-ethoxyvinyl)stannane (10.5 g, 29.0 mmol, 3.0 eq) and 2-bromo-3,5-difluoro-4-(4-methylpiperazin-1-yl)aniline (3 g, 9.80 mmol, 1.0 eq) in toluene (30 mL) was added Pd(PPh$_3$)$_4$ (1.13 g, 980 umol, 0.1 eq). The mixture was stirred at 120° C. for 16 hrs. LCMS showed compound 3 was consumed completely and one main peak with desired mass was detected. The reaction mixture was quenched by addition of KF solution (30 mL) at 20° C. and stirred for 2 hrs. The mixture was diluted with water (10 mL) and extracted with EtOAc (20 mL*3). The combined organic layers were washed with brine (50 mL), dried over Na$_2$SO$_4$, filtered and concentrated under reduced pressure to give intermediate 2-(1-ethoxyvinyl)-3,5-difluoro-4-(4-methylpiperazin-1-yl) aniline (8.8 g) as a black brown oil. 2. To a solution of 2-(1-ethoxyvinyl)-3,5-difluoro-4-(4-methylpiperazin-1-yl)aniline (8.8 g, 29.60 mmol, 1 eq) in H$_2$O (3.0 mL) was added HOAc (26.4 mL). The mixture was stirred at 20° C. for 3 hrs. LCMS showed the intermediate was consumed completely. The reaction mixture was quenched by addition NaHCO$_3$ aq (50 mL) and NaOH (20 mL) at 20° C. The resulting mixture was extracted with EtOAc (50 mL*4). The combined organic layers were washed with brine (80 mL), dried over Na$_2$SO$_4$, filtered and concentrated under reduced pressure to give a residue. The residue was purified by column chromatography (SiO$_2$, DCM/MeOH=50/1 to 30/31) to afford the title compound (0.68 g, 8.53% yield) as a yellow solid. $^1$H NMR (400 MHz, CHLOROFORM-d) δ=6.27 (br s, 2H), 6.11 (dd, J=2.0, 12.8 Hz, 1H), 3.10 (br d, J=4.0 Hz, 4H), 2.63-2.50 (m, 6H), 2.35 (s, 3H), 2.04 (s, 1H).

5-cyano-2-(methylthio)benzoyl chloride

Step 1, methyl 2-chloro-5-cyano-benzoate: To a solution of 2-chloro-5-cyano-benzoic acid (10 g, 55.0 mmol, 1.0 equiv.) was added SOCl$_2$ (82.0 g, 689.2 mmol, 50 mL, 12.5 equiv.). The reaction mixture was stirred at 80° C. for 1 hour. The reaction mixture was cooled to RT and concentrated under reduced. The residue was dissolved in THF (50 mL) and added to MeOH (50 mL). The reaction mixture was cooled to RT and quenched with a saturated aqueous solution of NaHCO$_3$ (100 mL) and extracted with ethyl acetate (3×50 mL). The combined organic layers were washed with brine, dried over Na$_2$SO$_4$, filtered, and concentrated under reduced pressure to afford the title compound (9 g, 84% yield) as a white solid. $^1$H NMR (400 MHz, CDCl$_3$) δ 8.15 (d, J=2.0 Hz, 1H), 7.70 (dd, J=2.0, 8.4 Hz, 1H), 7.60 (d, J=8.4 Hz, 1H), 3.98 (s, 3H).

Step 2,5-cyano-2-methylsulfanyl-benzoic acid: To a solution of NaSMe (35.83 g, 511 mmol, 2.5 equiv.) in DMF (400 mL) was added dropwise a solution of methyl 2-chloro-5-cyano-benzoate (40 g, 205 mmol, 1.0 equiv.) in DMF (400 mL) at 0° C. Then the mixture was stirred at 0° C. for 3 hours. The pH of the reaction mixture was adjusted to pH=1 with HCl (1M). The mixture was filtered and the filter cake was dried over under vacuum to afford the title compound (30 g, 76% yield) as a white solid. LCMS [M−1]=192.1. $^1$H NMR (400 MHz, DMSO-d6) δ 13.53 (br s, 1H), 8.21 (d, J=2.0 Hz, 1H), 7.92 (dd, J=2.0, 8.4 Hz, 1H), 7.51 (d, J=8.6 Hz, 1H), 2.46 (s, 3H).

Step 3, 5-cyano-2-(methylthio) benzoyl chloride: A solution of 5-cyano-2-(methylthio) benzoic acid (4.2 g, 22.0 mmol, 1.0 equiv.) in SOCl$_2$ (56 mL) was stirred at 80° C. for 1 hour. The mixture was concentrated under reduced pressure to afford the title compound (4.6 g, 99% yield) as a yellow solid. The product was used without further purification.

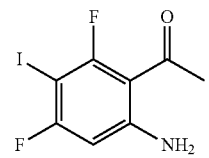

1-(6-amino-2,4-difluoro-3-iodo-phenyl)ethenone: To a solution of 1-(2-amino-4,6-difluoro-phenyl)ethanone (10.0 g, 58.4 mmol, 1.0 equiv.) in DCM (100 mL) was added N-iodosuccinimide (14.4 g, 64.2 mmol, 1.1 equiv.). The mixture was stirred at RT for 16 hours. The reaction mixture was diluted with water (100 mL) and extracted with DCM (2×200 mL). The combined organic layers were washed with brine, dried over Na$_2$SO$_4$, filtered, and concentrated under reduced pressure to give a residue. The residue was purified by silica gel column chromatography (0-33% ethyl acetate in petroleum ether) to afford the title compound (6.5 g, 37% yield) as a brown solid. LCMS [M+1]=297.7. $^1$H NMR (4(0) MHz, CHLOROFORM-d) δ 6.70-6.43 (m, 2H), 6.26 (dd, J=1.8, 9.6 Hz, 1H), 2.61 (d, J=9.0 Hz, 3H).

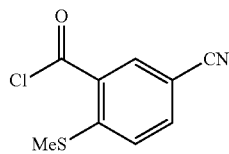 [SMILES: CSc1ccc(C#N)cc1C(=O)Cl]

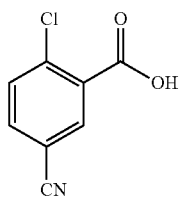 [SMILES: N#Cc1ccc(Cl)c(C(=O)O)c1]

2-chloro-5-cyanobenzoic acid: 2-chloro-5-iodobenzoic acid (6.0 g, 21.2 mmol, 1.0 equiv.) was combined with tert-butanol (18 g), water (24 g), potassium carbonate (2.94 g, 21.2 mmol, 1.0 equiv.), potassium ferrocyanide trihydrate (4.49 g, 10.6 mmol, 0.5 equiv.). The mixture was stirred for 1 hour before addition of tris(dibenzylideneacetone)dipalladium(0) (0.097 g, 0.1 mmol, 0.005 equiv.), 1,4-bis(diphenylphosphino)butane (0.091 g, 0.2 mmol, 0.01 equiv.) and a mixture of tert-butanol (6.0 g) and water (6.0 g). The mixture was adjusted to 75° C. for 17 hours before cooling to 20° C. Ammonium pyrrolidinedithiocarbamate (1.80 g, 11.0 mmol, 0.5 equiv.) was charged followed by water (1.8 g) and the mixture was adjusted to 45° C., and stirred for 20 hours. The mixture was cooled to 25° C., and filtered through diatomite and rinsed with water (18 g). The filtrate was extracted twice with methyl tert-butyl ether (2×18 g) and the aqueous layer was combined with ethyl acetate (54 g) and adjusted to 20° C. A 2N HCl solution (48 g) was added dropwise over 4 hours at 20° C. The mixture was stirred for one hour before the bottom aqueous layer was removed. The organic layer was washed with water (30 g) and treated with activated carbon (0.2 g) for 5 hours before removal by filtration and rinsing with ethyl acetate (12 g). The filtrate was concentrated to 12 mL under vacuum before charging acetone (24 g) and the process repeated. The solution was then concentrated to 12 mL before a final charge of acetone (12 g). The mixture was adjusted to 35° C. for 2 hours before charging 0.2N HCl (90 g) over 4 hours. The mixture was aged an additional 3 hours at 35° C. before adjusting to 25° C. over 5 hours and holding for 3 hours. The slurry was filtered and washed with water (12 g) before drying at 50° C. to deliver the title compound (2.7 g, 71% yield). $^1$H NMR (400 MHz, DMSO-$d_6$) δ 13.91 (br, 1H), 8.24 (d, J=4 Hz, 1H), 8.02 (m, 1H), 7.80 (d, J=8 Hz, 1H).

Example 1

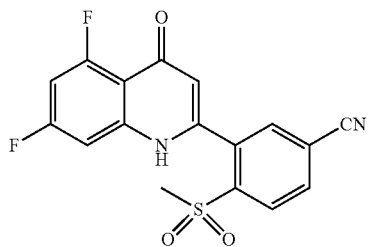 [SMILES: CS(=O)(=O)c1ccc(C#N)cc1-c1cc(=O)c2c(F)cc(F)cc2[nH]1]

3-(5,7-difluoro-4-oxo-1,4-dihydroquinolin-2-yl)-4-(methylsulfonyl)benzonitrile

Scheme 1, 2-chloro-5-cyanobenzoyl chloride:
A solution of 2-chloro-5-cyano-benzoic acid (2.5 g, 13.8 mmol) in SOCl$_2$ (25 mL) was stirred at 80° C. for 1 hour. The reaction mixture was then cooled to room temperature and concentrated under reduced pressure to afford the title compound (2.8 g, crude) as a yellow solid, the product was used directly in next step.

Scheme 1, Step 1, 142-amino-4,6-difluorophenyl)ethanone:
To a solution of 3,5-difluoroaniline (8.9 g, 68.9 mmol, 1.0 equiv.) in CH$_3$CN (85 mL) was added BCl$_3$ (1 M, 72.4 mL, 1.05 equiv.) at 0° C. Then AlCh; (10.1 g, 75.8 mmol, 4.1 mL, 1.1 equiv.) was added to the mixture in three portions and the mixture was then stirred at 80° C. for 16 hours. The mixture was cooled to 0° C., and then aqueous HCl (4M, 80 mL) was added and the mixture was stirred at 80° C. for 2 hours. The mixture was cooled to room temperature and extracted with EtOAc (2×150 mL). The combined organic layers were washed with saturated aqueous NaHCO$_3$ solution (2×50 mL), dried over Na$_2$SO$_4$, filtered, and concentrated under reduced pressure to afford the title compound (8.0 g, 68% yield) as a light-yellow solid. LCMS: calculated for [M+H]+ (C$_8$H$_7$F$_2$NO) requires m/z: =172.0, found m/z=172.1. $^1$H NMR (400 MHz, CDCl$_3$), δ 6.5 (br s, 2H), 6.0-6.2 (m, 2H), 2.6 (d, J=8.4 Hz, 3H).

Scheme 1, Step 2. N-(2-acetyl-3,5-difluorophenyl)-2-chloro-5-cyanobenzamide:
To a solution of 1-(2-amino-4,6-difluoro-phenyl)ethanone (2 g, 11.7 mmol, 1.0 equiv.) in THF (20 mL) was added NaH (467 mg, 11.7 mmol, 60%/6 dispersion in oil, 1.0 equiv.) at 0° C. The mixture was stirred for 30 minutes before the dropwise addition of a solution of 2-chloro-5-cyano-benzoyl chloride (2.6 g, 12.8 mmol, 1.1 equiv.) in THF (10 mL). The mixture was stirred at room temperature for 16 hours. The reaction mixture was quenched by the addition saturated aqueous NH$_4$Cl (15 mL) at 15° C., diluted with water (20 mL), and filtered. The filter cake was triturated with EtOAc (20 mL) and filtered to afford the title compound (2.4 g, 61% yield) as a white solid. LCMS: calculated for [M+H] (C$_{16}$H$_9$F$_3$N$_2$O$_2$) requires m/z=335.0, found m/z=335.0. $^1$H NMR (400 MHz, DMSO-$d_6$) δ 11.2 (s, 1H), 8.1 (d, J=2.0 Hz, 1H), 8.0 (dd, J=8.4, 2.2 Hz, 1H), 7.8 (d, J=8.4 Hz, 1H), 7.5-7.5 (m, 1H), 7.3 (ddd, J=11.2, 8.8, 2.2 Hz, 1H), 2.5-2.6 (m, 3H).

Scheme 1, Step 3, 4-chloro-3-(5,7-difluoro-4-oxo-1,4-dihydroquinolin-2-yl)benzonitrile To a solution of N-(2-acetyl-3,5-difluoro-phenyl)-2-chloro-5-cyano-benzamide (2.5 g, 7.5 mmol, 1.0 equiv.) in dioxane (40 mL) was added NaOH (3.0 g, 74.7 mmol, 10.0 equiv.). The mixture was stirred at 110° C. for 1.5 hours. The pH of the reaction mixture was adjusted to 5 with aqueous HCl (1 M) and then diluted with water (30 mL) and extracted with EtOAc (3×100 mL). The combined organic layers were washed with brine (2×100 mL), dried over Na$_2$SO$_4$, filtered, and concentrated under reduced pressure to afford a crude residue that was purified by preparative HPLC (column: Welch Xtimate C18 250×70 mm×10 um; mobile phase: 1545% acetonitrile in water (10 mM NH$_4$HCO$_3$)). This afforded the title compound (570 mg, 24% yield, 98% purity) as a white solid after concentration under reduced pressure. LCMS: calculated for [M+H]$^+$ (C$_{16}$H$_7$ClF$_2$N$_2$O) requires m/z=317.0, found m/z=317.0. $^1$H NMR (400 MHz, DMSO-$d_6$) δ 9.2-10.3 (m, 1H), 8.2 (d, J=2.0 Hz, 1H), 8.0 (dd, J=8.4, 2.0 Hz, 1H), 7.9 (d, J=8.4 Hz, 1H), 7.0-7.2 (m, 2H), 6.1 (s, 1H).

Scheme 1, Step 4, 3-(5,7-difluoro-4-oxo-1,4-dihydroquinolin-2-yl)-4-(methylsulfonyl)benzonitrile To a mixture of 4-chloro-3-(5,7-difluoro-4-oxo-1,4-dihydroquinolin-2-yl)benzonitrile (100 mg, 316 μmol, 1.0 equiv.) in DMSO (3 mL) were added sodium methanesulfinate (41.9 mg, 411 μmol, equiv.), K₃PO₄ (67.0 mg, 316 μmol, 1.0 equiv.), CuI (6.0 mg, 32 μmol, 0.1 equiv.) and quinolin-8-ol (4.6 mg, 32 μmol, 0.1 equiv.) at 20° C. under N₂. The mixture was stirred at 120° C. for 24 hours. The reaction mixture was diluted with H₂O (30 mL) and extracted with ethyl acetate (3×30 mL). The combined organic layers were washed with brine (20 mL), dried with anhydrous Na₂SO₄, filtered, and concentrated under vacuum. The residue was purified by preparative HPLC (column: Waters Xbridge BEH C18 100*30 mm*10 um; Mobile phase: 25%-55% acetonitrile in water (+NH₄HCO₃)) to afford the title compound (37.4 mg, 33% yield, 99.3% purity) as a white crystalline solid, characterized as crystalline Form A. LCMS [M+1]=361.0. ¹H NMR (400 MHz, METHANOL-d₄) δ 8.36 (d, J=8.4 Hz, 1H), 8.20 (dd, J=1.6, 8.4 Hz, 1H), 8.13 (d, J=1.4 Hz, 1H), 7.06 (br d, J=9.4 Hz, 1H), 6.99 (ddd, J=2.4, 9.4, 11.8 Hz, 1H), 6.31 (s, 1H), 3.20 (s, 3H).

Alternative Synthesis of 3-(5,7-difluoro-4-oxo-1,4-dihydroquinolin-2-yl)-4-(methylsulfonyl)benzonitrile

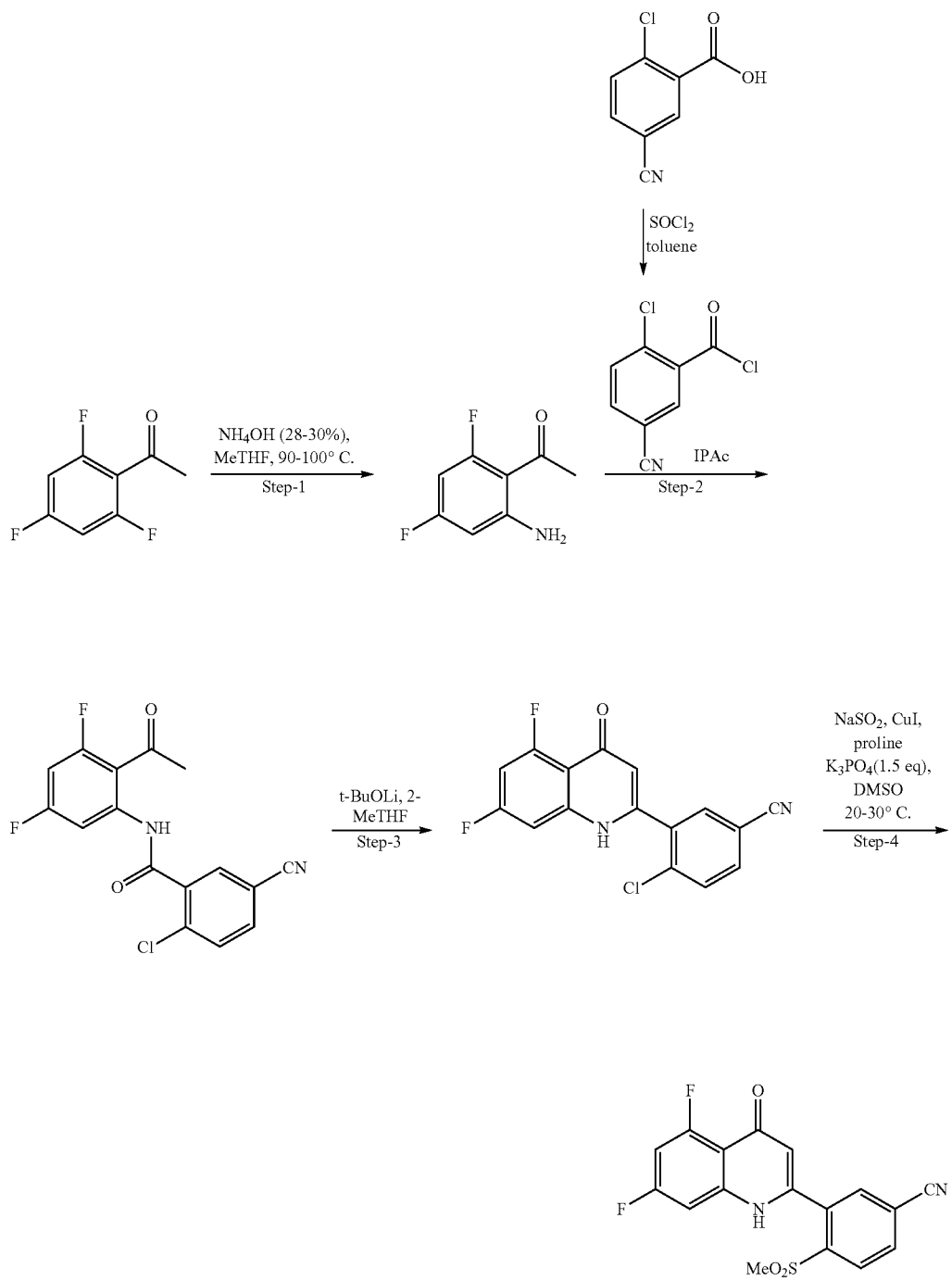

Step 1, 1-(2-amino-4,6-difluorophenyl)ethanone

A mixture of 1-(2,4,6-trifluorophenyl)ethan-1-one (10.0 g, 57.4 mmol, 1.0 equiv.) in 2-methyltetrahydrofuran (30 g) and 28% aqueous ammonium hydroxide (28.0 g, 459.5 mmol, 8.0 equiv.) was heated to 105° C. for 23 hours. The mixture was cooled to 25° C., and toluene (80 g) was charged. The layers were separated and the organic layer was concentrated to 30 mL under vacuum. Toluene (30 g) was charged to the organic layer before washing twice with 3N HCl (2×30 g) and once with 5% aqueous NaHCO$_3$ (30 g). The organic layer was concentrated to 20 mL under vacuum before charging isopropyl acetate (80 g). The mixture was again concentrated to 20 mL and isopropyl acetate (30 g) was charged to deliver the title compound as a solution in isopropyl acetate (82% assay yield).

Step 2, N-(2-acetyl-3,5-difluorophenyl)-2-chloro-5-cyanobenzamide

A solution of 2-chloro-5-cyano-benzoic acid (6.0 g, 33.0 mmol, 1.1 equiv.) in toluene was adjusted to 80° C., and SOCl$_2$ (6.9 g, 58.4 mmol, 2.0 equiv.) was charged over 1 hour. The mixture was stirred for 6 hours at 80° C., before cooling and concentrating under vacuum to 10 mL. Isopropyl acetate (35 g) was charged and the mixture was concentrated to 10 mL once again. The charge of isopropyl acetate (35 g) and concentration to 10 mL was repeated before a final charge of isopropyl acetate (10 g). The mixture was adjusted to 45° C. and a solution of 1-(2-amino-4,6-difluorophenyl)ethanone in isopropyl acetate (5.0 g, 29.2 mmol, 1.0 equiv., 35 mL as a solution in isopropyl acetate) was charged over 2 hours. The mixture was adjusted to 80° C., and stirred for 12 hours before cooling to 25° C., and filtering. The solids were rinsed twice with isopropyl acetate (2×25 g) and twice with n-heptane (2×25 g) before drying at 50° C. to deliver the title compound (8.7 g, 89% yield).

Step 3, 4-chloro-3-(5,7-difluoro-4-oxo-1,4-dihydroquinolin-2-yl)benzonitrile Lithium tert-butoxide (1.4 g, 17.9 mmol, 1.2 equiv.) was added to a mixture of N-(2-acetyl-3,5-difluorophenyl)-2-chloro-5-cyanobenzamide (5.0 g, 14.9 mmol, 1.0 equiv.) and 2-methyltetrahydrofuran (100 g). The mixture was adjusted to 75° C. for 22 hours before cooling to 20° C. Dimethyl sulfoxide (20 g) was charge and the mixture adjusted to 40° C. for 2 hours. A 1N HCl solution (50 g) was slowly added and the mixture stirred for an additional 3 hours at 40° C. The mixture was cooled to 5° C. over 3 hours and stirred for an additional 16 hours. The slurry was filtered and the solids washed twice with water (2×10 g) and twice with acetone (2×10 g). The wet solids were then slurry washed in acetone (40 g) at 50° C. for 3 hours before cooling to 5° C., and stirring for an additional 3 hours. The slurry was filtered and the solids rinsed with acetone (10 g). The solids were dried at 55° C. to deliver the title compound (4.8 g, 80% yield)

Figure 2:
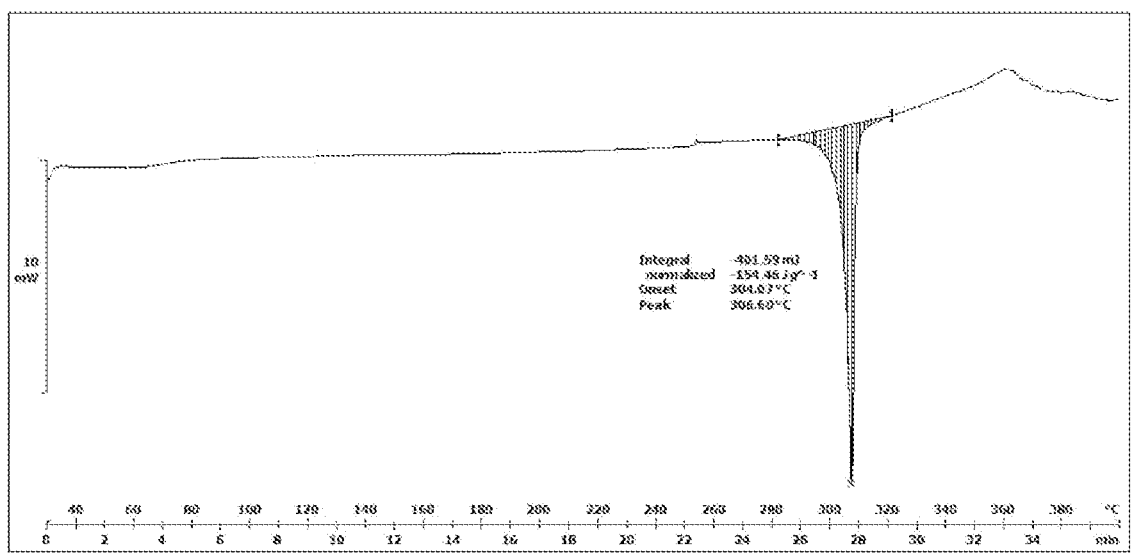
FIG. 2 depicts a differential scanning calorimetry (DSC) thermogram for Form A of 3-(5,7-difluoro-4-oxo-1,4-dihydroquinolin-2-yl)-4-(methylsulfonyl)benzonitrile.

Step 4, 3-(5,7-difluoro-4-oxo-1,4-dihydroquinolin-2-yl)-4-(methylsulfonyl)benzonitrile To a solution of 4-chloro-3-(5,7-difluoro-4-oxo-1,4-dihydroquinolin-2-yl)benzonitrile (10.0 g, 31.6 mmol, 1 equiv.) in dimethyl sulfoxide (65 g) was added sodium methanesulfinate (3.89 g, 37.9 mmol, 1.2 equiv.), tripotassium phosphate (10.1 g, 47.4 mmol, 1.5 equiv.), copper(I) iodide (0.60 g, 3.16 mmol, 0.1 equiv.) and L-proline (0.36 g, 3.16 mmol, 0.1 equiv.). The mixture was stirred at 25° C. for 4 hours then quenched with 5% aqueous ammonium hydroxide (50 g). The mixture was stirred for 4 hours before addition of 1N HCl (300 g) and an additional 12 hours of stirring. The solids were filtered and washed with water (2×50 g). The solids were then slurry washed in water (150 g) at 50° C. for 14 hours before cooling to 25° C. for filtration. The wet solids were then slurry washed in acetone (80 g) at 50° C. for 3 hours before cooling to 5° C. over 3 hours and ageing 2 hours before filtration and washing with acetone (20 g). The solids were dried at 50° C. to deliver the title compound (7.1 g, 61% yield). HRMS: calculated for [M+H]$^+$ (C$_{17}$H$_{10}$F$_2$N$_2$O$_3$S) requires m/z=361.0453, found m/z=361.0453. $^1$H NMR (500 MHz, MeOH-d$_4$) δ 8.50 (d, J=8.3 Hz, 1H), 8.33 (dd, J=8.3, 1.6 Hz, 1H), 8.26 (d, J=1.5 Hz, 1H), 7.20 (d, J=9.4 Hz, 1H), 7.14-7.10 (m, 1H), 6.46 (s, 1H), 3.34 (s, 3H). The XRPD pattern of the resulting product, 3-(5,7-difluoro-4-oxo-1,4-dihydroquinolin-2-yl)-4-(methylsulfonyl)benzonitrile, characterized as Form A, the XRPD for which is shown in FIG. 1. The DSC curve is shown in FIG. 2 and indicated an endothermic transition with onset of about 304° C.

The compounds in Table 2 were prepared following Scheme 1 using similar procedures to those described for Example 1.

TABLE 2

| Example number | Structure | IUPAC Name | $^1$H NMR | LCMS Exact Mass |
|---|---|---|---|---|
| 2 | 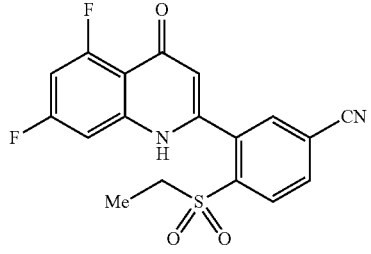 [SMILES: CCS(=O)(=O)c1ccc(C#N)cc1-c1cc(=O)c2c(F)cc(F)cc2[nH]1] | 3-(5,7-difluoro-4-oxo-1,4-dihydroquinolin-2-yl)-4-(ethylsulfonyl)-benzonitrile | (400 MHz, DMSO-d$_6$) δ12.17 (br d, J = 1.9 Hz, 1H), 8.34 (br d, J = 5.9 Hz, 2H), 8.28-8.23 (m, 1H), 7.28-7.04 (m, 2H), 6.16 (br d, J = 4.6 Hz, 1H), 2.09 (s, 1H), 1.15 (br t, J = 7.3 Hz, 3H). | Calculated m/z 375.1, found m/z 375.0 |

TABLE 2-continued

| Example number | Structure | IUPAC Name | ¹H NMR | LCMS Exact Mass |
|---|---|---|---|---|
| 3 | 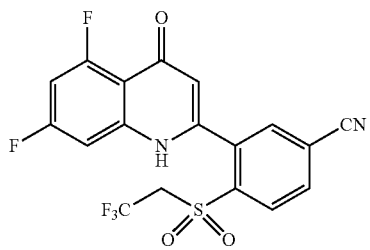 [SMILES: N#Cc1ccc(S(=O)(=O)CC(F)(F)F)c(-c2cc(=O)c3c(F)cc(F)cc3[nH]2)c1] | 3-(5,7-difluoro-6-(4-methylpiperazin-1-yl)-4-oxo-1,4-dihydroquinolin-2-yl)-4-(methylsulfonyl)-benzonitrile | (400 MHz, DMSO-$d_6$) δ 10.96 (br d, J = 1.1 Hz, 1H), 8.36-8.23 (m, 3H), 7.39 (br d, J = 11.8 Hz, 1H), 6.51-6.40 (m, 1H), 3.58 (br s, 2H), 3.46 (br d, J = 11.7 Hz, 2H), 3.40 (s, 3H), 3.37 (br s, 2H), 3.22-3.13 (m, 2H), 2.83 (br d, J = 4.4 Hz, 3H). | Calculated m/z 459.1, found m/z 459.1. |

Example 4

3-(5,7-difluoro-4-oxo-1,4-dihydroquinolin-2-yl)-4-((2,2,2-trifluoroethyl)sulfonyl)-benzonitrile Scheme 2, step 1, 3-(5,7-difluoro-4-oxo-1,4-dihydroquinolin-2-yl-4-((2,2,2-trifluoroethyl)thio)benzonitrile: To a solution of 2,2,2-trifluoroethane-1-thiol (780 mg, 6.72 mmol, 596 μL, 1.0 equiv.) in THF (1 mL) was added NaH (242 mg, 6.05 mmol, 60% purity, 0.9 equiv.). The mixture was stirred at 20° C. for 1 hr. The reaction mixture was concentrated under reduced pressure to remove solvent to give sodium 2,2,2-trifluoroethanethiolate (850 mg, crude) as a white solid. Then, to a solution of 4-chloro-3-(5,7-difluoro-4-oxo-1,4-dihydroquinolin-2-yl)benzonitrile (600 mg, 1.89 mmol, 1.0 equiv.) and sodium 2,2,2-trifluoroethanethiolate (809 mg, 6.63 mmol, 3.5 equiv.) in DMSO (10 mL) was added $K_2CO_3$ (576 mg, 4.17 mmol, 2.2 equiv.) and CuI (36 mg, 190 μmol, 0.1 equiv.). The mixture was stirred at 100° C. for 16 hrs. The residue was diluted with water (10 mL) and extracted with EtOAc (3×10 mL). The combined organic layers were washed with brine (5 mL), dried over anhydrous $Na_2SO_4$, filtered, and concentrated under reduced pressure. The residue was purified by silica gel column chromatography (gradient of 5:1 to 1:1 petroleum ether:ethyl acetate) to afford the title compound (120 mg, crude) as yellow solid which used directly in next step without any more purification.

Scheme 2, Step 2, 3-(5,7-difluoro-4-oxo-1,4-dihydroquinolin-2-yl)-4-((2,2,2-trifluoroethyl)sulfonyl)-benzonitrile To a mixture of 3-(5,7-difluoro-4-oxo-1,4-dihydroquinolin-2-yl)-4-((2,2,2-trifluoroethyl)thio)benzonitrile (100 mg, 252 μmol, 1 equiv.) in acetone (1 mL), $H_2O$ (0.6 mL), MeOH (0.75 mL) and THF (0.75 mL) was added Oxone (930 mg, 1.51 mmol, 3.0 equiv.) in two portions at 20° C. under $N_2$. The mixture was stirred at 60° C. for 24 hours. The reaction was diluted with water (10 mL) and extracted with EtOAc (3×10 mL). The combined organic layers were washed with brine (5 mL), dried over anhydrous $Na_2SO_4$, filtered, and concentrated under reduced pressure. The residue was purified by preparative HPLC (Column: Phenomenex Luna 80*30 mm*3 um; Mobile phase: 20-50% acetonitrile in water (+HCl)) to afford the title compound (5.4 mg, 4.9% yield, 97.9% purity) as a white solid. LCMS [M+1]=328.9. ¹H NMR (400 MHz, DMSO-$d_6$) δ 8.40-8.34 (m, 2H), 8.33-8.27 (m, 1H), 8.21 (d, J=8.4 Hz, 1H), 7.23 (br s, 1H), 6.65-6.20 (m, 1H), 5.12 (q, J=9.8 Hz, 2H).

Example 5

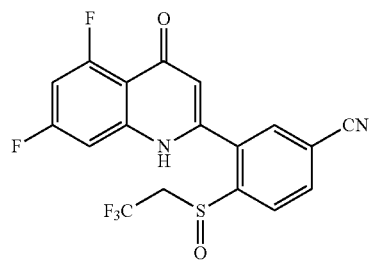 [SMILES: N#Cc1ccc(S(=O)CC(F)(F)F)c(-c2cc(=O)c3c(F)cc(F)cc3[nH]2)c1]

Scheme 2, step 2, 3-(5,7-difluoro-4-oxo-1,4-dihydroquinolin-2-yl)-4-((2,2,2-trifluoroethyl)sulfinyl)benzonitrile:

To a mixture of 3-(5,7-difluoro-4-oxo-1,4-dihydroquinolin-2-yl)-4-((2,2,2-trifluoroethyl)thio)benzonitrile (50 mg, 126 μmol, 1.0 equiv.) in acetone (1 mL) $H_2O$ (0.6 mL) MeOH (0.75 mL) and THF (0.75 mL) was added Oxone (77.6 mg, 126 μmol, 1.0 equiv.) at 20° C. under $N_2$. The mixture was stirred at 20° C. for 16 hours. The reaction was diluted with water (5 mL) and extracted with EtOAc (3×5 mL). The combined organic layers were washed with brine (5 mL), dried over anhydrous $Na_2SO_4$, filtered, and concentrated under reduced pressure. The residue was purified by preparative HPLC (Column: Phenomenex Luna 80*30 mm*3 um; Mobile phase: 25-55% acetonitrile in water (+HCl)) to afford the title compound (15.0 mg, 28% yield, 97.7% purity) as white solid. LCMS [M+1]=412.9. ¹H NMR (400 MHz, DMSO-d$_6$) δ 12.50-11.93 (m, 1H), 8.58-8.18 (m, 3H), 7.51-7.08 (m, 2H), 6.54-5.88 (m, 1H), 4.85-3.96 (m, 2H).

Example 6

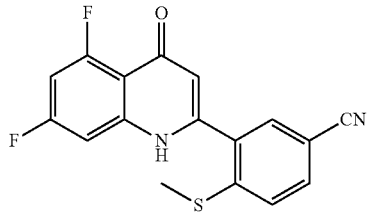 [SMILES: CSc1ccc(C#N)cc1-c1cc(=O)c2c(F)cc(F)cc2[nH]1]

Scheme 2, step 1, 3-(5,7-difluoro-4-oxo-1,4-dihydroquinolin-2-yl)-4-(methylthio)benzonitrile:

To a mixture of 4-chloro-3-(5,7-difluoro-4-oxo-1,4-dihydroquinolin-2-yl)benzonitrile (500 mg, 1.58 mmol, 1.0 equiv.) in DMSO (8 mL) was added NaSMe (387 mg, 5.53 mmol, 3.5 equiv.). K$_2$CO$_3$ (480 mg, 3.48 mmol, 2.2 equiv.) and CuI (30 mg, 158 μmol, 0.1 eq) at 20° C. under N$_2$, and then the mixture was stirred at 100° C. for 16 hours under N$_2$. The reaction mixture was added to water (50 mL) and stirred at 25° C. for 30 mins. then extracted with ethyl acetate (3×30 mL). The combined organic layers were washed with brine (20 mL), dried with anhydrous Na$_2$SO$_4$, filtered, and concentrated under reduced pressure. The residue was purified by preparative HPLC (Column: Phenomenex Luna C18 75*30 mm*3 um, Mobile phase: 30-60% acetonitrile in water (+formic acid)) to afford the title compound (220 mg, 41% yield, 96.9% purity) as a white solid. LCMS [M+1]=329.0. ¹H NMR (400 MHz, DMSO-d$_6$) δ 12.00 (br s, 1H), 8.05-7.90 (m, 2H), 7.60 (d, J=8.4 Hz, 1H), 7.23-7.02 (m, 2H), 5.99 (s, 1H), 2.54 (s, 3H).

Example 7

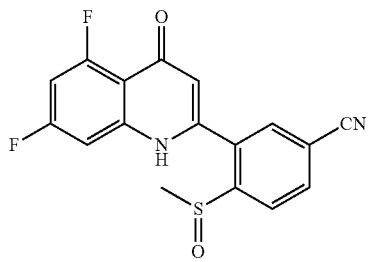 [SMILES: CS(=O)c1ccc(C#N)cc1-c1cc(=O)c2c(F)cc(F)cc2[nH]1]

Scheme 2, step 2, 3-(5,7-difluoro-4-oxo-1,4-dihydroquinolin-2-yl)-4-(methylsulfinyl)benzonitrile:

To a mixture of 3-(5,7-difluoro-4-oxo-1,4-dihydroquinolin-2-yl)-4-(methylthio)benzonitrile (50 mg, 152 μmol, 1.0 equiv.) in DCM (2 mL) was added m-CPBA (31 mg, 152 μmol, 85% purity, 1.0 equiv.) at 20° C., and then the mixture was stirred at 20° C. for 1 hour under N$_2$. The reaction mixture was quenched by the addition of a saturated aqueous solution of NaHSO$_3$ (20 mL) at 25° C., and then diluted with NaHCO$_3$ (20 mL) and extracted with DCM (3×10 mL). The combined organic layers were dried over Na$_2$SO$_4$, filtered, and concentrated under reduced pressure. The crude product was triturated with MTBE (5 mL) to afford the title compound (30 mg, 43% yield, 98.6% purity) as a white solid. LCMS [M+1]=345.0. ¹H NMR (400 MHz, METHANOL-d$_4$) δ 8.37 (br d, J=8.2 Hz, 1H), 8.25-8.16 (m, 2H), 7.35-7.22 (m, 1H), 7.13-7.03 (m, 1H), 6.85-6.54 (m, 1H), 3.03-2.80 (m, 3H).

Example 8

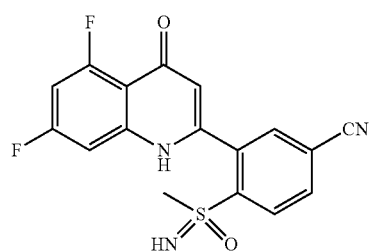

Scheme 2, step 2, 3-(5,7-difluoro-4-oxo-1,4-dihydroquinolin-2-yl)-4-(S-methylsulfonimidoyl)benzonitrile:

To a mixture of 3-(5,7-difluoro-4-oxo-1,4-dihydroquinolin-2-yl)-4-(methylthio)benzonitrile (50 mg, 152 μmol, 1.0 equiv.) in MeOH (1 mL) was added ammonium carbamate (59.4 mg, 761 μmol, 5.0 equiv.) at 20° C., then PhI(OAc)$_2$ (123 mg, 381 μmol, 2.5 equiv.) in MeOH (0.5 mL) was added to the mixture dropwise. The resulting mixture was stirred at 20° C. for 16 hours. The reaction mixture was concentrated under reduced pressure. The residue was purified by preparative HPLC (column: Phenomenex Luna C18 75*30 mm*3 um; Mobile phase: 1-40% acetonitrile in water (+formic acid)-ACN) to afford the title compound (22.6 mg, 37.6% yield, 99.8/o purity) as a yellow solid. LCMS [M+1]= 360.1. ¹H NMR (400 MHz, METHANOL-d$_4$) δ 8.41 (d, J=8.2 Hz, 1H), 8.17 (dd, J=1.8, 8.2 Hz, 1H), 8.09 (d, J=1.6 Hz, 1H), 7.11-6.92 (m, 2H), 6.30 (s, 1H), 3.21 (s, 3H).

Example 9

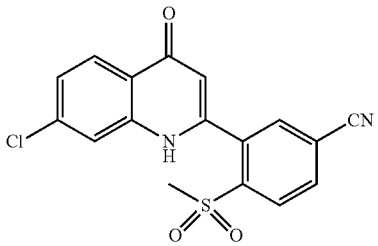 [SMILES: CS(=O)(=O)c1ccc(C#N)cc1-c1cc(=O)c2ccc(Cl)cc2[nH]1]

3-(7-chloro-4-oxo-1,4-dihydroquinolin-2-yl)-4-(methylsulfonyl)benzonitrile

Step 1, 1-(2-amino-4-chlorophenyl)ethanone: To a solution of 1-(4-chloro-2-nitrophenyl)ethanone (35 g, 175 mmol, 1.0 equiv.) in H$_2$O (350 mL) and acetic acid (350 mL) was added iron (0) (39.1 g, 701 mmol, 4.0 equiv.). The mixture was stirred at 100° C. for 2 hours. The suspension was filtered through a pad of Celite and the filter cake was washed with ethyl acetate (3×100 ml). The filtrate was concentrated under reduced pressure. The residue was diluted with ethyl acetate (300 mL) and H$_2$O (500 mL), and the layers were separated. The aqueous layer was extracted with ethyl acetate (2×300 mL). The combined organic layers were then washed with saturated aqueous NaHCO$_3$, brine, dried over anhydrous Na$_2$SO$_4$, filtered, and concentrated under reduced pressure to afford the title compound (27.7 g, crude) as a black-brown solid. This material was used in next step without further purification. LCMS [M+1]=170.2. $^1$H NMR (400 MHz, CHLOROFORM-d) δ 7.61 (d, J=8.6 Hz, 1H), 6.64 (s, 1H), 6.59 (br d, J=8.6 Hz, 1H), 6.39 (br s, 2H), 2.54 (s, 3H).

Step 2, N-(2-acetyl-5-chlorophenyl)-5-cyano-2-(methylthio)benzamide: To a solution of 1-(2-amino-4-chlorophenyl)ethenone (6.7 g, 39.6 mmol, 1.0 equiv.) in isopropyl acetate (300 mL) was added 5-cyano-2-methylsulfanyl-benzoyl chloride (8.4 g, 39.6 mmol, 1.0 equiv.). The mixture was stirred at 80° C. for 6 hours. The mixture was cooled to RT and filtered. The filter cake was washed with ethyl acetate (500 mL). The filter cake was dried under vacuum and triturated with MeOH at 25° C. for 0.5 hours to afford the title compound (10 g, 70% yield) as a white solid. LCMS [M+1]=345.0. $^1$H NMR (400 MHz, DMSO-d$_6$) δ 11.90 (s, 1H), 8.49 (d, J=2.0 Hz, 1H), 8.14-8.05 (m, 2H), 7.97 (dd, J=1.8, 8.4 Hz, 1H), 7.60 (d, J=8.6 Hz, 1H), 7.39 (dd, J=2.2, 8.5 Hz, 1H), 2.64 (s, 3H), 2.52 (s, 3H).

Step 3, 3-(7-chloro-4-oxo-1,4-dihydroquinolin-2-yl)-4-(methylthio)benzonitrile: To a solution of N-(2-acetyl-5-chlorophenyl)-5-cyano-2-(methylthio)benzamide (9.8 g, 28.4 mmol, 1.0 equiv.) in 2-MeTHF (300 mL) was added LiOH (4.0 g, 171 mmol, 6.0 equiv.). The mixture was stirred at 110° C. for 24 hours. The mixture was cooled to RT and the pH was adjusted to pH=3 with aqueous 1M HCl. The brown solid that precipitated during the pH adjustment was filtered off and washed with H$_2$O (600 mL), and then dried under vacuum. Trituration with acetonitrile at RT for 0.5 hours afforded the title compound (6.0 g, crude) as a light-yellow solid. LCMS [M+1]=327.1. $^1$H NMR (400 MHz, DMSO-d$_6$) δ 8.12 (d, J=8.8 Hz, 1H), 8.01-7.94 (m, 2H), 7.65-7.56 (m, 2H), 7.40 (dd, J=1.8, 8.7 Hz, 1H), 6.14 (s, 1H), 2.54 (s, 3H).

Step 4, 3-(7-chloro-4-oxo-1,4-dihydroquinolin-2-yl)-4-(methylsulfonyl)-benzonitrile: To a solution of 3-(7-chloro-4-oxo-1,4-dihydroquinolin-2-yl)-4-(methylthio)benzonitrile (5.0 g, 15.3 mmol, 1.0 equiv.) in H$_2$O (160 mL), CHCl$_3$ (80 mL), and acetonitrile (80 mL) was added NaIO$_4$ (9.8 g, 45.9 mmol, 3.0 equiv.) and ruthenium trichloride (317 mg, 1.5 mmol, 0.1 equiv.) at RT under N$_2$. The mixture was stirred at RT for 16 hours. The suspension was filtered through a filter paper and the pad cake was washed with MeOH (3×150 mL). The filtrate was concentrated under reduced pressure. The residue was triturated with first with MTBE and then with MeOH at RT for 0.5 hours to afford the title compound (2.4 g, 45% yield) as a white solid. LCMS [M+1]=359.0. $^1$H NMR (400 MHz, DMSO-d$_6$) δ 12.10 (br s, 1H), 8.33 (br d, J=10.2 Hz, 3H), 8.13 (br d, J=7.8 Hz, 1H), 7.54 (br s, 11H), 7.40 (br d, J=6.8 Hz, 1H), 6.21 (br s, 1H), 3.35-3.28 (m, 3H).

Example 10

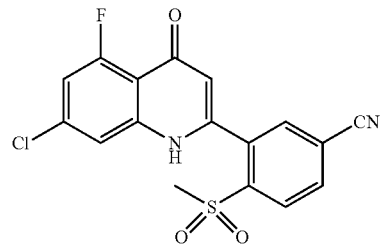 [SMILES: CS(=O)(=O)c1ccc(C#N)cc1-c1cc(=O)c2c(F)cc(Cl)cc2[nH]1]

3-(7-chloro-5-fluoro-4-oxo-1,4-dihydroquinolin-2-yl)-4-methylsulfonyl)-benzonitrile Step 1, 142-amino-4-chloro-6-fluorophenyl)ethanone: To a solution of 3-chloro-5-fluoroaniline (20 g, 137 mmol, 1.0 equiv.) in p-xylene (40 mL) was added BCl$_3$ (1 M, 182.7 mL, 1.3 equiv.) at 0-5° C. over 2 hours. The mixture was warmed up to RT within 0.5 hours and stirred at RT for 10 minutes. Then acetonitrile (57.8 mL, 1.10 mol, 8 equiv.) was added dropwise at RT over 20 minutes. The mixture was stirred at RT for 10 minutes, then p-xylene (45 mL) was added. Then AlCl$_3$ (10.2 g, 76.9 mmol, 0.5 equiv.) was added and the reaction mixture was stirred at RT for 1 hour and then stirred at 75-77° C. for another 12 hours. Then aqueous HCl (4 N, 200 mL) was added to the mixture and the mixture was stirred at 80° C. for 4 hours. The mixture was poured into water (800 mL) and extracted with ethyl acetate (1.5 L). The organic phase was washed with brine (100 mL), dried with anhydrous Na$_2$SO$_4$, filtered, and concentrated under reduced pressure. The residue was purified by silica gel column chromatography (50:1 to 20:1 petroleum ether:ethyl acetate) to afford the title compound (4.6 g, 18% yield) as a light-yellow solid. LCMS [M+1]=188.0/190.0. $^1$H NMR (400 MHz, CHLOROFORM-d) δ 6.53-6.41 (m, 2H), 6.36 (dd, J=2.0, 11.8 Hz, 2H), 2.58 (d, J=8.4 Hz, 3H).

Step 2, N-(2-acetyl-5-chloro-3-fluorophenyl)-5-cyano-2-(methylthio)benzamide: To a solution of 1-(2-amino-4-chloro-6-fluorophenyl)ethanone (4.1 g, 21.8 mmol, 1 equiv.) in isopropyl acetate (48 mL) was added 5-cyano-2-(methylthio)benzoyl chloride (4.6 g, 21.8 mmol, 1.0 equiv.). The mixture was stirred at 80° C. for 2 hours. The mixture was cooled to RT and concentrated under reduced pressure. The residue was triturated with acetonitrile (30 mL) at RT to afford the title compound (5.5 g, 70% yield) as a white solid. LCMS [M+1]=363.0/364.0. $^1$H NMR (400 MHz, DMSO-d$_6$) δ 11.03 (s, 1H), 8.00 (d, J=1.8 Hz, 1H), 7.95 (dd, J=1.8, 8.4 Hz, 1H), 7.63 (s, 1H), 7.57 (d, J=8.4 Hz, 1H), 7.47 (dd, J=1.8, 10.5 Hz, 1H), 3.42 (s, 1H), 2.54 (d, J=3.8 Hz, 3H).

Step 3, 3-(7-chloro-5-fluoro-4-oxo-1,4-dihydroquinolin-2-yl)-4-(methylthio)benzonitrile: To a solution of N-(2-acetyl-5-chloro-3-fluorophenyl)-5-cyano-2-(methylthio) benzamide (5 g, 13.7 mmol, 1.0 equiv.) in 2-MeTHF (50 mL) was added LiOH (495 mg, 20.6 mmol, 1.5 equiv.). The mixture was stirred at 100° C. for 16 hours. The mixture was cooled to RT. The pH of the reaction mixture was adjusted to pH=3 with aqueous 2N HCl. The precipitate that formed during the pH adjustment was filtered off and the filter cake was dried under vacuum. The residue was triturated with ethyl acetate at RT to afford the title compound (3.8 g, 78% yield) as a white solid. LCMS [M+1]=345.0/347.0. $^1$H NMR (400 MHz, DMSO-d$_6$) δ 12.01 (br s, 1H), 8.01-7.95 (m, 2H), 7.60 (d, J=8.2 Hz, 1H), 7.40 (br s, 1H), 7.25 (br d, J=10.8 Hz, 1H), 6.02 (br s, 1H), 2.54 (s, 3H).

Step 4, 3-(7-chloro-5-fluoro-4-oxo-1,4-dihydroquinolin-2-yl)-4-(methylsulfonyl)benzonitrile: To a solution of 3-(7-chloro-5-fluoro-4-oxo-1,4-dihydroquinolin-2-yl)-4-(methylthio)-benzonitrile (3.2 g, 9.2 mmol, 1.0 equiv.) in acetone (16.8 mL), H$_2$O (9.6 mL), THF (12 mL) and MeOH (12 mL) was added Oxone (28.5 g, 46.4 mmol, 5.0 equiv.). The mixture was stirred at 50° C. for 16 hours. The reaction mixture was cooled to RT and quenched with an aqueous solution of Na$_2$SO$_3$ (3 equiv.). The reaction mixture was diluted with H$_2$O (100 mL) and filtered. The filter cake was washed with water and dried under reduced pressure. Trituration of the crude residue with MTBE (2×150 mL) at RT and then trituration with MeOH (2×150 mL) at RT afforded the title compound (2.3 g, 65.4% yield) as off-white solid. LCMS [M+1]=377.0/379.0. $^1$H NMR (400 MHz, DMSO-d$_6$) δ 12.15 (br s, 1H), 8.43-8.22 (m, 3H), 7.62-7.17 (m, 2H), 6.38-6.02 (m, 1H), 3.47-3.25 (m, 3H).

Example 11

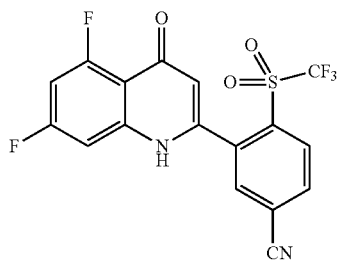 [SMILES: N#Cc1ccc(S(=O)(=O)C(F)(F)F)c(-c2cc(=O)c3c(F)cc(F)cc3[nH]2)c1]

3-(5,7-difluoro-4-oxo-1,4-dihydroquinolin-2-yl)-4-((trifluoromethylsulfonyl)benzonitrile Step 1, methyl 5-cyano-2-iodo-benzoate: To a solution of 5-cyano-2-iodo-benzoic acid (4.0 g, 14.6 mmol, 1.0 equiv.) in MeOH (30 mL) was added H$_2$SO$_4$ (1.2 mL, 22.8 mmol, 1.6 equiv.). The mixture was stirred at 80° C. for 16 hours. The reaction mixture was concentrated under reduced pressure. The residue was diluted with water (30 mL) and extracted with ethyl acetate (3×30 mL). The combined organic layers were washed with brine, dried over anhydrous Na$_2$SO$_4$, filtered, and concentrated under reduced pressure to afford the title compound (4.0 g, 95% yield) as a yellow solid. $^1$H NMR (400 MHz, CHLOROFORM-d) δ 8.16 (d, J=8.2 Hz, 1H), 8.08 (d, J=2.0 Hz, 1H), 7.40 (dd, J=2.0, 8.2 Hz, 1H), 3.98 (s, 3H).

Step 2, Methyl 5-cyano-2-(trifluoromethylsulfanyl) benzoate: To a mixture of methyl 5-cyano-2-iodo-benzoate (1.5 g, 5.2 mmol, 1.0 equiv.) and trifluoromethylsulfanylsilver (1.1 g, 5.2 mmol, 1.0 equiv.) in DMF (15 mL) was added copper(I)bromide (75.0 mg, 523 μmol, 0.1 equiv.) and 1,10-phenanthroline (188.3 mg, 1.1 mmol, 0.2 equiv.) at RT under N$_2$. The mixture was stirred at 80° C. for 16 hours under N$_2$. The reaction mixture was poured into ice-water (250 mL) and stirred for 30 minutes. The aqueous phase was extracted with ethyl acetate (2×100 mL). The combined organic layers were washed with aqueous NaHCO$_3$ (2×100 ml), dried with anhydrous Na$_2$SO$_4$, filtered, and concentrated under reduced pressure. The residue was purified by silica gel column chromatography (100:1 to 14:1 petroleum ether:ethyl acetate) to afford the title compound (1.2 g, 88% yield) as white solid. $^1$H NMR (400 MHz, CHLOROFORM-d) δ 8.31 (d, J=1.5 Hz, 1H), 7.89-7.74 (m, 2H), 4.00 (s, 3H).

Step 3, 5-cyano-2-(trifluoromethylsulfanyl) benzoic acid: To a mixture of methyl 5-cyano-2-(trifluoromethylsulfanyl) benzoate (1.2 g, 4.6 mmol, 1.0 equiv.) in THF (12 mL) and H$_2$O (3 mL) was added LiOH—H$_2$O (231 mg, 5.5 mmol, 1.2 equiv.) at RT under N$_2$. The mixture was stirred at RT for 2 hours. The pH of the reaction mixture was adjusted to pH=4-5 with aqueous 1 N HCl. The THF was removed under reduced pressure. The precipitate was filtered off and dried under vacuum to afford the title compound (1.0 g, 90% yield) as white solid. LCMS [M–1]=246.0. $^1$H NMR (400 MHz, DMSO-d$_6$) δ 14.93-13.99 (m, 1H), 8.41 (d, J=1.8 Hz, 1H), 8.15 (dd, J=2.0, 8.6 Hz, 1H), 7.85 (d, J=8.2 Hz, 1H).

Step 4, N-(2-acetyl-3,5-difluoro-phenyl)-5-cyano-2-(trifluoromethylsulfanyl) benzamide: SOCl$_2$ (5 mL) was added to a flask containing 5-cyano-2-(trifluoromethylsulfanyl) benzoic acid (1.0 g, 4.1 mmol, 1.0 equiv.) at RT under N$_2$. The mixture was stirred at 80° C. for 2 hours. The mixture was concentrated under reduced pressure to afford 5-cyano-2-(trifluoromethylsulfanyl)benzoyl chloride (1.1 g, crude) as white solid which was used in the next phase of the reaction without further purification.

To a mixture of 1-(2-amino-4,6-difluoro-phenyl) ethanone (644 mg, 3.8 mmol, 1.0 equiv.) in isopropyl acetate (15 mL) was added 5-cyano-2-(trifluoromethylsulfanyl) benzoyl chloride (1.1 g, 4.14 mmol, 1.1 equiv.) at RT under N$_2$. The mixture was stirred at 80° C. for 16 hours. The mixture was concentrated under reduced pressure and the crude product was triturated with acetonitrile at RT for 30 minutes to afford the title compound (1.2 g, 77% yield) as white solid LCMS [M+1]=401.1. $^1$H NMR (400 MHz, CHLOROFORM-d) δ 12.63 (br s, 1H), 8.53-8.43 (m, 1H), 8.01 (d, J=1.8 Hz, 1H), 7.94 (d, J=8.4 Hz, 1H), 7.83 (dd, J=1.8, 8.4 Hz, 1H), 6.73 (ddd, J=2.6, 8.2, 12.2 Hz, 1H), 2.72 (d, J=8.6 Hz, 3H).

Step 5, 3-(5,7-difluoro-4-oxo-1H-quinolin-2-yl)-4-(trifluoromethylsulfanyl) benzonitrile: To a mixture of N-(2-acetyl-3,5-difluoro-phenyl)-5-cyano-2-(trifluoromethylsulfanyl) benzamide (1.2 g, 3.0 mmol, 1.0 equiv.) in 2-MeTHF (18 mL) was added LiOH (71.8 mg, 3.0 mmol, 1.0 equiv.) in at RT under N$_2$. The mixture was stirred at 80° C. for 32 hours under N$_2$. The reaction mixture was diluted with water (10 mL) and then concentrated to remove 2-MeTHF. The pH of the mixture was adjusted to pH=4-5 with aqueous 1N HCl. The precipitate that formed during the pH adjustment was filtered off and then triturated with acetonitrile at RT for 30 minutes to afford the title compound (930 mg, 80% yield) as a white solid. LCMS [M+1]=383.0. $^1$H NMR (400 MHz, DMSO-d$_6$) δ 12.10 (br s, 1H), 8.34 (d, J=1.4 Hz, 1H), 8.17 (br d, J=11.8 Hz, 2H), 7.34-6.92 (m, 2H), 6.11 (br s, 1H).

Step 6, 3-(5,7-difluoro-4-oxo-1H-quinolin-2-yl)-4-(trifluoromethylsulfonyl)benzonitrile: To a mixture of 3-(5,7-difluoro-4-oxo-1H-quinolin-2-yl)-4-(trifluoromethylsulfanyl) benzonitrile (700 mg, 1.8 mmol, 1.0 equiv.) and RuCl$_3$ (38 mg, 183.1 μmol, 0.1 equiv.) in CHCl$_3$ (7 mL), ACN (7 mL) and H$_2$O (14 mL) was added NaIO$_4$ (1.2 g, 5.5 mmol, 3.0 equiv.) in one portion at RT under N$_2$. The mixture was stirred at RT for 16 hours. The reaction was quenched with a saturated aqueous solution of Na$_2$SO$_3$ (15 mL) and stirred at RT for 1 hour. The aqueous phase was extracted with ethyl acetate (2×50 mL). The combined organic layers were washed with brine, dried with anhydrous Na$_2$SO$_4$, filtered, and concentrated under reduced pressure. The residue was purified by preparative HPLC (column: Phenomenex luna C18 100×40 mm×3 um; mobile phase: 25-65% acetonitrile in water (+formic acid modifier)) to afford the title compound (100 mg, 13% yield) as white solid. LCMS [M+1] = 415.0. ¹H NMR (400 MHz, METHANOL-d₄) δ 8.51 (d, J=8.2 Hz, 11H), 8.39-8.28 (m, 2H), 7.08-6.95 (m, 2H), 6.22 (br s, 1H).

Example 12

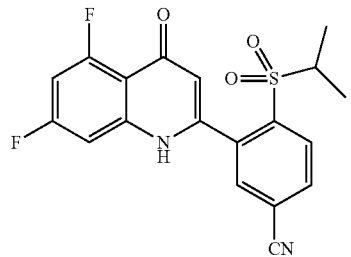 [SMILES: CC(C)S(=O)(=O)c1ccc(C#N)cc1-c1cc(=O)c2c(F)cc(F)cc2[nH]1]

3-(5,7-difluoro-4-oxo-1,4-dihydroquinolin-2-yl)-4-(isopropylsulfonyl)benzonitrile Step 1, 5-cyano-2-isopropylsulfanyl-benzoic acid: To a solution of propane-2-thiol (2.3 mL, 25.5 mmol, 2.5 equiv.) in DMF (20 mL) was added NaH (1.0 g, 25.5 mmol, 2.5 equiv.; 60% dispersion in oil). The reaction mixture was stirred at RT for 1 hour before methyl 2-chloro-5-cyano-benzoate (2.0 g, 10.2 mmol, 1.0 equiv.) was added to the mixture. The resulting mixture was stirred at RT for 2 hours. The reaction was quenched with H₂O (2 equiv.) and the pH of the solution was adjusted to pH=4 with aqueous 1N HCl. The precipitate that formed during the pH adjustment was filtered off and triturated with MTBE at RT for 10 minutes to afford the title compound (2.0 g, 88% yield) as a pale-yellow solid. LCMS: [M−1]=220.1. ¹H NMR (400 MHz, CHLOROFORM-d) δ 8.39 (d, J=2.0 Hz, 1H), 7.71 (dd, J=1.8, 8.4 Hz, 1H), 7.47 (d, J=8.4 Hz, 1H), 3.60 (td, J=6.6, 13.4 Hz, 1H), 1.45 (d, J=6.6 Hz, 6H).

Step 2, N-(2-acetyl-3,5-difluoro-phenyl)-5-cyano-2-isopropylsulfanyl-benzamide: A solution of 5-cyano-2-isopropylsulfanyl-benzoic acid (500 mg, 2.2 mmol, 10 equiv.) in SOCl₂ (5.0 mL) was stirred at 80° C. for 1 hour. The reaction mixture was concentrated under reduced pressure to afford 5-cyano-2-isopropylsulfanyl-benzoyl chloride (542 mg, crude) as a yellow solid. This material was used in the next phase of the reaction without further purification. To a solution of 1-(2-amino-4,6-difluoro-phenyl)ethanone (350 mg, 2.05 mmol, 1.0 equiv.) in isopropyl acetate (10 mL) was added 5-cyano-2-isopropylsulfanyl-benzoyl chloride (539 mg, 2.2 mmol, 1.1 equiv.). The mixture was stirred at 80° C. for 16 hours. The reaction mixture was concentrated, and the resulting residue was triturated with acetonitrile at RT for 10 minutes to afford the title compound (570 mg, 74% yield) as a pale-yellow solid. LCMS [M+1]=375.1. ¹H NMR (400 MHz, METHANOL-d₄) δ 8.73 (d, J=1.6 Hz, 1H), 8.67 (dd, J=1.8, 8.2 Hz, 1H), 8.54-8.44 (m, 2H), 7.96 (ddd, J=2.4, 9.0, 11.4 Hz, 1H), 4.51 (td, J=6.6, 13.2 Hz, 1H), 3.36 (d, J=5.4 Hz, 3H), 2.08 (d, J=6.8 Hz, 6H).

Step 3, 3-(5,7-difluoro-4-oxo-1H-quinolin-2-yl)-4-isopropylsulfanyl-benzonitrile: To a solution of N-(2-acetyl-3,5-difluoro-phenyl)-5-cyano-2-isopropylsulfanyl-benzamide (470 mg, 1.2 mmol, 1.0 equiv.) in dioxane (10 mL) was added LiOH (45 mg, 1.8 mmol, 1.5 equiv.). The reaction mixture was stirred at 110° C. for 10 hours. The pH of the reaction mixture was adjusted pH=1 with aqueous 1M HCl. The precipitate that formed during the pH adjustment was filtered off and then triturated with acetonitrile at RT for 10 minutes to afford the title compound (400 mg, 89% yield) as a white solid. LCMS [M+1]=357.1. ¹H NMR (400 MHz, DMSO-d₆) δ 12.15-11.98 (m, 1H), 7.98-7.90 (m, 2H), 7.71 (d, J=8.2 Hz, 1H), 7.12 (m, 2H), 5.97 (s, 1H), 3.75 (m, 1H), 1.26 (d, J=6.6 Hz, 6H).

Step 4, 3-(5,7-difluoro-4-oxo-1,4-dihydroquinolin-2-yl-4-(isopropylsulfonyl)benzonitrile: To a solution of 3-(5,7-difluoro-4-oxo-1H-quinolin-2-yl)-4-isopropylsulfanyl-benzonitrile (150 mg, 421 μmol, 1.0 equiv.) in DCM (5.0 mL) was added m-CPBA (256 mg, 1.2 mmol, 3.0 equiv.: 85% purity). The reaction mixture was stirred at RT for 16 hours. The reaction mixture was quenched by the addition of Na₂SO₃ (300 mg) in H₂O (5.0 mL). The reaction mixture was extracted with DCM (2×5 mL). The combined organic layers were dried over Na₂SO₄, filtered, and concentrated under reduced pressure. The residue was purified by preparative HPLC (column: Phenomenex luna C18 80×40 mm×3 um; mobile phase: 2545% acetonitrile in water (+HCl modifier)) to afford the title compound (41.2 mg, 25% yield) as a white solid. LCMS [M+1]=389.1. ¹H NMR (400 MHz, METHANOL-d₄) δ8.33-8.29 (dd, J=8.0 Hz, 11H), 8.24-8.19 (dd, J=1.4 Hz, J=8.0 Hz, 1H), 8.16 (d, J=1.4 Hz, 1H), 7.14-7.08 (m, 1H), 7.07-7.02 (m, 1H), 6.37 (s, 1H), 3.40 (quin, J=6.8 Hz, 1H), 1.26-1.20 (m, 6H).

Example 13

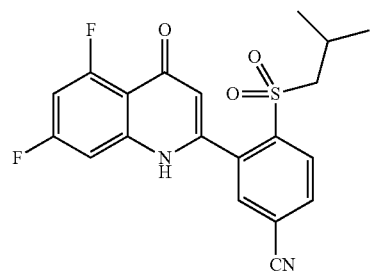 [SMILES: CC(C)CS(=O)(=O)c1ccc(C#N)cc1-c1cc(=O)c2c(F)cc(F)cc2[nH]1]

3-5,7-difluoro-4-oxo-1,4-dihydroquinolin-2-yl-4-(isobutylsulfonyl)benzonitrile This compound was prepared in a similar manner to that described for Example 12, using 2-methylpropane-1-thiol as the starting material. LCMS [M+1]=403.1. ¹H NMR (400 MHz, DMSO-d₆) δ 8.20 (s, 2H), 8.14 (s, 1H), 7.03 (br d, J=10.0 Hz, 1H), 6.95 (br s, 1H), 6.11 (s, 1H), 3.58 (br d, J=6.0 Hz, 2H), 2.09-1.98 (m, 1H), 0.0% (d, J=6.6 Hz, 6H).

Example 14

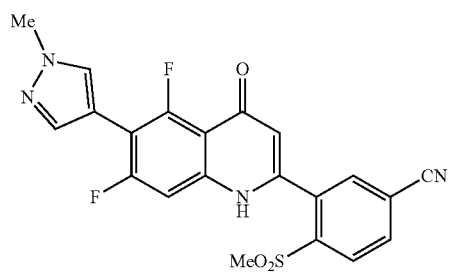 [SMILES: Cn1cc(-c2c(F)cc3[nH]c(-c4cc(C#N)ccc4S(C)(=O)=O)cc(=O)c3c2F)cn1]

3-(5,7-difluoro-6(1-methyl-1H-pyrazol-4-yl-4-oxo-1,4-dihydroquinolin-2-yl-4-(methylsulfonyl)benzonitrile Step 1, 1-[6-amino-2,4-difluoro-3-(1-methylpyrazol-4-yl)phenyl]ethenone: To a solution of 1-methyl-4-(4,4,5,5-tetramethyl-1,3,2-dioxaborolan-2-yl)pyrazole (500 mg, 2.4 mmol, 1.0 equiv.) and 1-(6-amino-2,4-difluoro-3-iodo-phenyl)ethanone (714 mg, 2.4 mmol, 1.0 equiv.) in dioxane (7.5 mL) was added a solution of $K_2CO_3$ (664 mg, 4.8 mmol, 2.0 equiv.) in $H_2O$ (2.5 mL) and Pd(dppf)Cl $CH_2Cl_2$ (196 mg, 240 μmol, 0.1 equiv.) at RT under $N_2$. The mixture was stirred at 80° C. for 16 hours under $N_2$. The residue was poured into ice-water (100 mL) and ethyl acetate (100 mL) stirred for 10 minutes. The mixture was filtered through a pad of celite. The organic phase was separated and washed with brine (2×20 mL), dried with anhydrous $Na_2SO_4$, filtered, and concentrated under reduced pressure. The residue was purified by silica gel column chromatography (100:1 to 5:1 petroleum ether:ethyl acetate). The crude product was triturated with petroleum ether at RT for 10 minutes to afford the title compound (200 mg, 33% yield) as yellow solid. LCMS [M+1]=252.2. $^1$H NMR (400 MHz, CHLOROFORM-d) δ 7.84 (s, 1H), 7.71 (s, 1H), 6.40 (br t, J=5.6 Hz, 2H), 6.25 (dd, J=1.6, 12.6 Hz, 1H), 3.97 (s, 3H), 2.64 (d, J=9.0 Hz, 3H).

Step 2, N-[2-acetyl-3,5-difluoro-4-(1-methylpyrazol-4-yl)phenyl]-2-chloro-5-cyano-benzamide: To a mixture of 1-[6-amino-2,4-difluoro-3-(1-methylpyrazol4-yl)phenyl]ethanone (200 mg, 796 μmol, 1.0 equiv.) in isopropyl acetate (1.5 mL) was added 2-chloro-5-cyano-benzoyl chloride (195 mg, 876 μmol, 1.1 equiv.) at RT under $N_2$. The mixture was stirred at 80° C. for 8 hours. The mixture was filtered and concentrated under reduced pressure. The residue was triturated with water and then acetonitrile at RT to afford the title compound (300 mg, 91% yield) as light-yellow solid. LCMS [M+1]=415.1. $^1$H NMR (400 MHz, DMSO-$d_6$) δ 11.03 (s, 11H), 8.20 (s, 11H), 8.11 (d, J=1.9 Hz, 1H), 8.05 (dd, J=2.0, 8.3 Hz, 11H), 7.88-7.81 (m, 2H), 7.50 (d, J=11.2 Hz, 1H), 3.93 (s, 3H), 2.59 (d, J=3.8 Hz, 3H).

Step 3, 4-chloro-3-[5,7-difluoro-6-(1-methylpyrazol-4-yl)-4-oxo-1H-quinolin-2-yl]benzonitrile: To a mixture of N-[2-acetyl-3,5-difluoro-4-(1-methylpyrazol-4-yl)phenyl]-2-chloro-5-cyano-benzamide (300 mg, 723 μmol, 1.0 equiv.) in dioxane (1 mL) was added LiOH (19.0 mg, 796 μmol, 1.1 equiv.) at RT under $N_2$. The mixture was stirred at 110° C. for 12 hours. The residue was poured into ice-water (100 mL), stirred for 30 minutes and filtered. The filter cake was triturated with acetonitrile at RT to afford the title compound (240 mg, 82% yield) as light-yellow solid. LCMS [M+1]=397.0. $^1$H NMR (400 MHz, DMSO-$d_6$) δ 12.10 (s, 11H), 8.25 (d, J=1.8 Hz, 11H), 8.19 (s, 11H), δ 09 (dd, J=2.0, 8.4 Hz, 11H), 7.93 (d, J=8.4 Hz, 1H), 7.85 (s, 1H), 7.22 (d, J=11.5 Hz, 1H), 6.06 (d, J=1.5 Hz, 1H), 3.95-3.91 (m, 3H).

Step 4, 3-[5,7-difluoro-6-(1-methylpyrazol-4-yl)-4-oxo-1H-quinolin-2-yl]-4-methylsulfonyl-benzonitrile: To a mixture of sodium methanesulfinate (37.0 mg, 363 μmol, 1.2 equiv.), 4-chloro-3-[5,7-difluoro-6-(1-methylpyrazol-4-yl)-4-oxo-1H-quinolin-2-yl]benzonitrile (120 mg, 302 μmol, 1.0 equiv.) and $K_3PO_4$ (96.3 mg, 453.7 μmol, 1.5 equiv.) in DMF (3 mL) was added CuI (5.8 mg, 30.2 μmol, 0.1 equiv.) at RT under $N_2$. The mixture was stirred at 100° C. for 2 hours. The mixture was quenched by the addition of aqueous ammonia solution and then stirred for 30 minutes. The pH of the mixture was adjusted to pH=3-4 with aqueous 1N HCL. The precipitate that formed during the pH adjustment was filtered off and then purified by preparative HPLC (column: Phenomenex Luna C18 200×40 mm×10 um; mobile phase: 20-50% acetonitrile in water (+formic acid modifier)) to afford the title compound (60 mg, 45% yield) as white solid. LCMS [M+1]=441.0. $^1$H NMR (400 MHz, DMSO-$d_6$+$D_2O$) δ 8.28 (s, 2H), 8.25-8.21 (m, 1H), 8.21-8.14 (m, 1H), 7.85 (s, 1H), 7.45-7.07 (m, 1H), 6.23-6.16 (m, 1H), 3.91 (s, 3H), 3.31 (br s, 3H).

Example 15

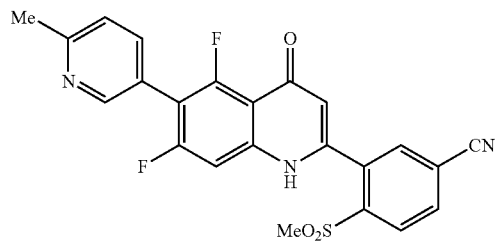 [SMILES: Cc1ccc(-c2c(F)cc3[nH]c(-c4cc(C#N)ccc4S(C)(=O)=O)cc(=O)c3c2F)cn1]

3-(5,7-difluoro-6-(6-methylpyridin-3-yl)-4-oxo-1,4-dihydroquinolin-2-yl)-4-(methylsulfonyl)benzonitrile This compound was prepared in a similar manner to that described for Example 14 using 2-methyl-5-(4,4,5,5-tetramethyl-1,3,2-dioxaborolan-2-yl)pyridine and 1-(6-amino-2,4-difluoro-3-iodophenyl)ethanone as the starting materials. LCMS [M+1]=452.0. $^1$H NMR (400 MHz, DMSO-$d_6$) δ 12.55-11.94 (m, 1H), 8.57 (br s, 1H), 8.40-8.26 (m, 3H), 7.85 (br d, J=7.6 Hz, 1H), 7.43 (d, J=8.0 Hz, 1H), 7.37-7.11 (m, 1H), 6.45-5.90 (m, 1H), 3.32 (s, 3H), 2.55 (s, 3H).

Biochemical and Cellular Assays

PPARγ-NCOR1 Recruitment Assay:

Compound potency ($EC_{50}$) and maximal extent of NCOR1 recruitment to PPARG were assessed a TR-FRET binding assay measuring association of a biotinylated NCOR1 ID2 peptide (Biotin-GHSFADPASNLGLE-DIIRKALMG-amide) to PPARG/RXRA LBD heterodimer. Specifically, a 20 microliters of TR-FRET master mix consisting of 2 nM WT PPARG LBD (E. coli expressed, His-TEV-Q203-Y477: Uniprot ID P37231-2), 2 nM WT RXRA LBD or mutant S427F RXRA LBD (E. coli expressed, Flag-TEV-E228-T462; P19793-1), 50 nM NCOR1, 80 nM Rosiglitazone, 25 nM streptavidin-d2 (Cisbio) and 0.3 nM Anti-His Tb (Cisbio) in 25 mM MOPS pH 7.4, 25 mM KCl, 1 mM EDTA, 0.01% BSA, 0.01% Tween-20 and 1 mM TCEP was added to 384-well plates containing duplicate 10-point dose response titrations of compounds in 60 nL DMSO (0.3% f.c. DMSO (v/v)). Mixtures were incubated for 3 hours and read in an EnVision plate reader (Perkin Elmer) with Ex/Em 615/665. To determine the potency ($EC_{50}$) and extent of NCOR1 recruitment, TR-FRET ratios were normalized to the average ratio of DMSO control wells (0%) and to the average maximum ratio for positive control compound (T0070907 (2-chloro-5-nitro-N-4-pyridinyl-benzamide); defined as 100%) in CDD Vault and analyzed using the Levenberg-Marquardt algorithm.

PPARγ-MED1 Blockade Assay:

Compound potency (ICs) and maximal extent of MED1 repulsion to PPARG were assessed a TR-FRET binding assay measuring association of a biotinylated MED1 LxxLL peptide (Biotin-VSSMAGNTKNHPMLMNLLKDNPAQ-amide) to PPARG/RXRA LBD heterodimer. Specifically, a 20 microliters of TR-FRET master mix consisting of 2 nM WT PPARG LBD (E. coli expressed, His-TEV-Q203-Y477; Uniprot ID P37231-2), 2 nM WT RXRA LBD (E. coli expressed, Flag-TEV-E228-T462; P19793-1), 350 nM NCOR1, 80 nM Rosiglitazone, 175 nM streptavidin-d2 (Cisbio) and 0.3 nM Anti-His Tb (Cisbio) in 25 mM MOPS pH 7.4, 25 mM KCl, 1 mM EDTA, 0.01% BSA, 0.01% Tween-20 and 1 mM TCEP was added to 384-well plates containing duplicate 10-point dose response titrations of compounds in 60 nL DMSO (0.3% DMSO f.c. (viv)). Mixtures were incubated for 3 hours and read in an EnVision plate reader (Perkin Elmer) with Ex/Em 615/665. To determine the potency (ICso) and extent of MED1 repulsion. TR-FRET ratios were normalized to the average ratio of DMSO control wells (0%) and to the average minimum ratio for positive control compound (GW9662 (2-chloro-5-nitrobenzanilide); defined as 100%/6) in CDD Vault and analyzed using the Levenberg-Marquardt algorithm.

Bladder Cancer Pharmacodynamic Assay 5637 (PPARG amplified) and HT1197 (RXRA S427F mutation) cells were used for assessment of modulation of PPARG target genes using quantitative PCR. Cells were treated for 24 hours with PPARG inverse agonists prior to analysis of FABP4 (IDT, Cat: Hs.PT 58.20106818) and ANGPTL4 (IDT, Cat: Hs.PT 58.25480012) expression, with expression of the housekeeping gene TBP (IDT, Cat: Hs.PT 58v.39858774) used to normalize expression across samples. Quantitative PCR was performed using an ABI QuantStudio 7 Flex Reaction system. Data were analyzed and reported relative to DMSO control using the comparative Ct method (ΔΔCt).

Table 3

For the PPARG-NCOR recruitment assay the $EC_{50}$ is expressed as follows, A: <10 nM, B: 10-100 nM, C: 100-1.000 nM. D: 1,000-10,000 nM, E: >10.000 nM. The % NCOR recruitment is expressed as follows, A: >100% (>the control compound, T907), B: <100% (<the control compound, T907).

For the PPARG-MED1 recruitment assay the $EC_{50}$ is expressed as follows, A: <10 nM, B: 10-100 nM, C: 100-1,000 nM, D: 1,000-10,000 nM, E: >10,000 nM. The % MED1 blockade is expressed as follows, A: >100%(>the control compound, GW9662), B: <100% (<the control compound. GW9662).

For the HT1197 cell assay the $EC_{50}$ is expressed as follows, A: <10 nM, B: 10-100 nM. C: 100-1,000 nM, D: 1,000-10,000 nM, E: >10,000 nM, ND: not determined. The % inhibition of ANGPTL4, a PPARG target gene, at 100 nM compound concentration is expressed as percentage of a DMSO control experiment.

| Example number | PPARG-NCOR recruitment assay $EC_{50}$-% NCOR recruitment relative to T907 | PPARG-MED1 blockade assay $EC_{50}$-% MED1 blockade relative to GW9662 | HT1197 cell assay $EC_{50}$-% inhibition of ANGPTL4 @ 100 nM |
|---|---|---|---|
| 1 | C-A | C-A | 1.3 nM-88 |
| 2 | C-A | C-A | ND-86 |
| 3 | C-A | C-A | ND-66 |
| 4 | C-A | C-A | ND-14 |
| 5 | D-A | D-A | ND-15 |
| 6 | E-ND | E-ND | ND-17 |
| 7 | D-A | E-A | ND-26 |
| 8 | C-A | C-A | ND-84 |
| 9 | B-A | B-A | 0.9 nM-85 |
| 10 | B-A | B-A | 1.6 nM-89 |
| 11 | A-A | A-A | 0.07 nM-88 |
| 12 | E-B | E-B | ND-67 |
| 13 | D-B | D-B | ND-77 |
| 14 | B-A | B-A | ND-89 |
| 15 | B-A | B-A | ND-68 |

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of the structural formula:

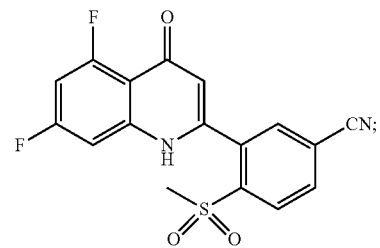 [SMILES: CS(=O)(=O)c1ccc(C#N)cc1-c1cc(=O)c2c(F)cc(F)cc2[nH]1]

or a pharmaceutically acceptable salt thereof.

2. A pharmaceutical composition comprising the compound of claim 1, or a pharmaceutically acceptable salt thereof; and a pharmaceutically acceptable carrier.

3. A method of treating urothelial cancer in a subject comprising administering to the subject a therapeutically effective amount of the compound of claim 1 or a pharmaceutically acceptable salt thereof.

4. Crystalline Form A of compound of the structural formula:

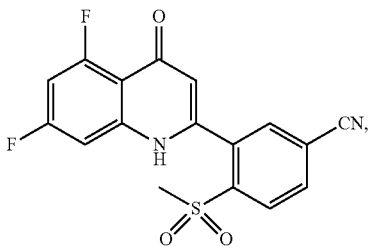 [SMILES: CS(=O)(=O)c1ccc(C#N)cc1-c1cc(=O)c2c(F)cc(F)cc2[nH]1]

wherein the crystalline form is characterized by at least three x-ray powder diffraction peaks at 2Θ angles selected from 6.1°, 9.3°, 12.7°, 18.8°, and 19.8°.

5. The crystalline Form A of claim 4, wherein the crystalline form is characterized by at least four x-ray powder diffraction peaks at 2Θ angles selected from 6.1°, 9.3°, 12.7°, 18.8°, and 19.8°.

6. The crystalline Form A of claim 5, wherein the crystalline form is characterized by x-ray powder diffraction peaks at 2Θ angles selected from 6.10, 9.3°, 12.7°, 18.8°, and 19.8°.

7. The crystalline Form A of claim 5, wherein the crystalline form is characterized by x-ray powder diffraction peaks at 2Θ angles selected from 6.10, 9.3°, and 12.7°.

8. The crystalline Form A of claim 5, wherein the crystalline form is characterized by x-ray powder diffraction peaks at 2Θ angles selected from 6.10, 9.3°, 12.7°, and 19.8°.

9. The crystalline Form A of claim 5, wherein the crystalline form is characterized by x-ray powder diffraction peaks at 2Θ angles selected from 6.1°, 9.3°, 12.7°, 17.7°, 18.8°, 19.8°, and 22.2°.

10. A pharmaceutical composition comprising the compound of claim 5, or a pharmaceutically acceptable salt thereof; and a pharmaceutically acceptable carrier.

11. A method of treating urothelial cancer in a subject comprising administering to the subject a therapeutically effective amount of the compound of claim 5 or a pharmaceutically acceptable salt thereof.

* * * * *

UNITED STATES PATENT AND TRADEMARK OFFICE
CERTIFICATE OF CORRECTION

PATENT NO. : 11,820,747 B2
APPLICATION NO. : 18/130121
DATED : November 21, 2023
INVENTOR(S) : Jonathan E. Wilson et al.

Page 1 of 2

It is certified that error appears in the above-identified patent and that said Letters Patent is hereby corrected as shown below:

In the Claims

Claim 6, at Column 46, Line 1, recites:
"The crystalline Form A of claim 5, wherein"
Please replace with the following:
"The crystalline Form A of claim 4, wherein"

Claim 7, at Column 46, Line 5, recites:
"The crystalline Form A of claim 5, wherein"
Please replace with the following:
"The crystalline Form A of claim 4, wherein"

Claim 8, at Column 46, Line 8, recites:
"The crystalline Form A of claim 5, wherein"
Please replace with the following:
"The crystalline Form A of claim 4, wherein"

Claim 9, at Column 46, Line 12, recites:
"The crystalline Form A of claim 5, wherein"
Please replace with the following:
"The crystalline Form A of claim 4, wherein"

Claim 10, at Column 46, Line 16-17, recites:
"A pharmaceutical composition comprising the compound of claim 5, or"
Please replace with the following:
"A pharmaceutical composition comprising the compound of claim 4, or"

Claim 11, at Column 46, Line 21, recites:
"effective amount of the compound of claim 5, or"

Signed and Sealed this
Sixth Day of February, 2024

Katherine Kelly Vidal
*Director of the United States Patent and Trademark Office*

Please replace with the following:
"effective amount of the compound of claim 4, or"